US009315582B2

(12) United States Patent
Seon et al.

(10) Patent No.: US 9,315,582 B2
(45) Date of Patent: Apr. 19, 2016

(54) ANTI-ENDOGLIN ANTIBODIES AND KNOCKIN MICE EXPRESSING NOVEL HUMAN/MOUSE CHIMERIC ENDOGLIN

(75) Inventors: Ben K. Seon, Williamsville, NY (US); Hirofumi Toi, Hokkaido (JP)

(73) Assignee: Health Research, Inc., Buffalo, NY (US)

( * ) Notice: Subject to any disclaimer, the term of this patent is extended or adjusted under 35 U.S.C. 154(b) by 48 days.

(21) Appl. No.: 14/001,201

(22) PCT Filed: Feb. 23, 2012

(86) PCT No.: PCT/US2012/026298
§ 371 (c)(1),
(2), (4) Date: Nov. 4, 2013

(87) PCT Pub. No.: WO2012/148538
PCT Pub. Date: Nov. 1, 2012

(65) Prior Publication Data
US 2014/0044724 A1 Feb. 13, 2014

Related U.S. Application Data

(60) Provisional application No. 61/445,970, filed on Feb. 23, 2011, provisional application No. 61/445,971, filed on Feb. 23, 2011.

(51) Int. Cl.
| C07K 16/00 | (2006.01) |
| C07K 16/18 | (2006.01) |
| A61K 39/395 | (2006.01) |
| C07K 16/30 | (2006.01) |
| C07K 16/28 | (2006.01) |
| A01K 67/027 | (2006.01) |
| C07K 14/705 | (2006.01) |
| C12N 15/85 | (2006.01) |
| A61K 39/00 | (2006.01) |

(52) U.S. Cl.
CPC ............ *C07K 16/30* (2013.01); *A01K 67/0278* (2013.01); *C07K 14/70596* (2013.01); *C07K 16/2896* (2013.01); *C12N 15/85* (2013.01); *A01K 2207/15* (2013.01); *A01K 2217/072* (2013.01); *A01K 2227/105* (2013.01); *A01K 2267/0375* (2013.01); *A61K 2039/505* (2013.01)

(58) Field of Classification Search
None
See application file for complete search history.

(56) References Cited
U.S. PATENT DOCUMENTS

| 5,660,827 A | 8/1997 | Thorpe et al. |
| 5,928,641 A | 7/1999 | Seon |
| 6,190,660 B1 | 2/2001 | Seon |
| 6,200,566 B1 | 3/2001 | Seon |
| 6,372,958 B1 | 4/2002 | Li et al. |
| 7,097,836 B1 | 8/2006 | Seon |
| 7,691,374 B2 | 4/2010 | Seon |

FOREIGN PATENT DOCUMENTS

WO 2010032059 3/2010

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Allinson et al., Generation of a floxed allele of the mouse endoglin gene, Genesis, vol. 45, No. 6, Jun. 1, 2007, pp. 391-395. Jun. 1, 2007.
Mancini et al., Endoglin is required for myogenic differentiation potential of neural crest stem cells, Developmental Biology, vol. 308, No. 2, Aug. 10, 2007, pp. 520-533. Aug. 10, 2007.
Volkel et al., Targeting of immunoliposomes to endothelial cells using a single-chain Fv fragment directed against human endoglin (CD105), Biochimica et Biophysica ACTA—Biomembranes, vol. 1663, No. 1-2, May 27, 2004, pp. 158-166. May 27, 2004.
Toi et al., Facilitation of endoglin-targeting cancer therapy by development/utilization of a novel genetically engineered mouse model expressing humanized endoglin (CD105), International Journal of Cancer, vol. 136, No. 2, May 28, 2014, pp. 452-461. May 28, 2014.
Tsujie et al., Effective anti-angiogenic therapy of established tumors in mice by naked anti-human endoglin (CD105 antibody) . . . , International Journal of Oncology 29: 1087-1094 (2006).
Uneda et al., Anti-endoglin monoclonal antibodies are effective for suppressing metastasis and the primary tumors by targeting tumor vasculature, Int. J. Cancer: 125, 1446-1453 (2009).
Takahashi, N., et al., Antiangiogenic therapy of established tumors in human skin/severe combined immunodeficiency mouse chimeras by anti-endoglin (CD105) monoclonal antibodies, and synergy between anti-endoglin antibody and cyclophosphamide, Cancer Research, 2001, vol. 61, No. 21, pp. 7846-7854.
Seon, B.K., et al., Endoglin-targeted cancer therapy, Current Drug Delivery, Jan. 2011, vol. 8, No. 1, pp. 135-143.

(Continued)

*Primary Examiner* — Christine J Saoud
*Assistant Examiner* — Jon M Lockard
(74) *Attorney, Agent, or Firm* — Hodgson Russ LLP

(57) ABSTRACT

Provided are compositions and methods that relate to prophylaxis and therapy of angiogenesis associated disease and includes novel knockin mice which express novel human/mouse chimeric endoglin, vectors for use in making such mice, and murine embryonic stem cells comprising the novel human/mouse transgene. Also provided are anti-human endoglin monoclonal antibodies (mAbs) which can be used as antiangiogenic agents for prophylaxis or therapy of human tumor angiogenesis and human angiogenesis-associated diseases having excessive vascularization. The mAbs do not cross react with murine endoglin. Also provides are methods for using the anti-human endoglin mAbs for prophylaxis or therapy of human tumor angiogenesis and for angiogenesis-associated diseases having excessive vascularization.

7 Claims, 19 Drawing Sheets

(56) References Cited

OTHER PUBLICATIONS

She, X., et al., Synergy between anti-endoglin (CD105) monoclonal antibodies and TFG-β in suppression of growth of human endothelial cells, Int. J. Cancer, 2004, vol. 108, No. 2, pp. 251-257.

Pichuantes, S., et al., Mapping epitopes to distinct regions of the extracellular domain of endoglin using bacterially expressed recombinant fragments, Tissue Antigens, 1997, vol. 50, No. 3, pp. 265-276.
She, Positional and functional epitope mapping of endoglin, a proliferation-associated antigen of human endothelial cells, Dissertation, State University of New York, Buffalo. Jan. 29, 2003.

* cited by examiner

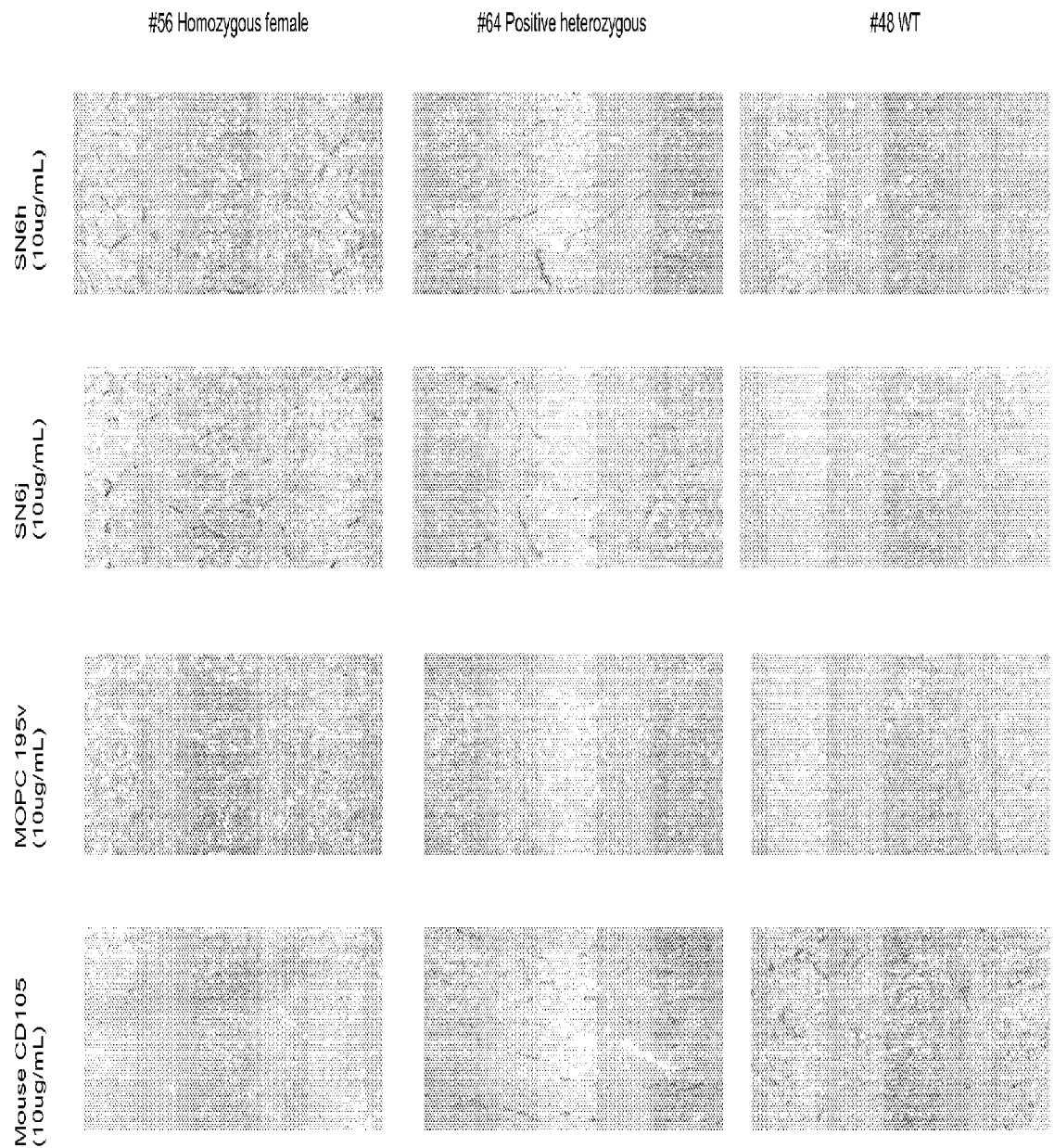

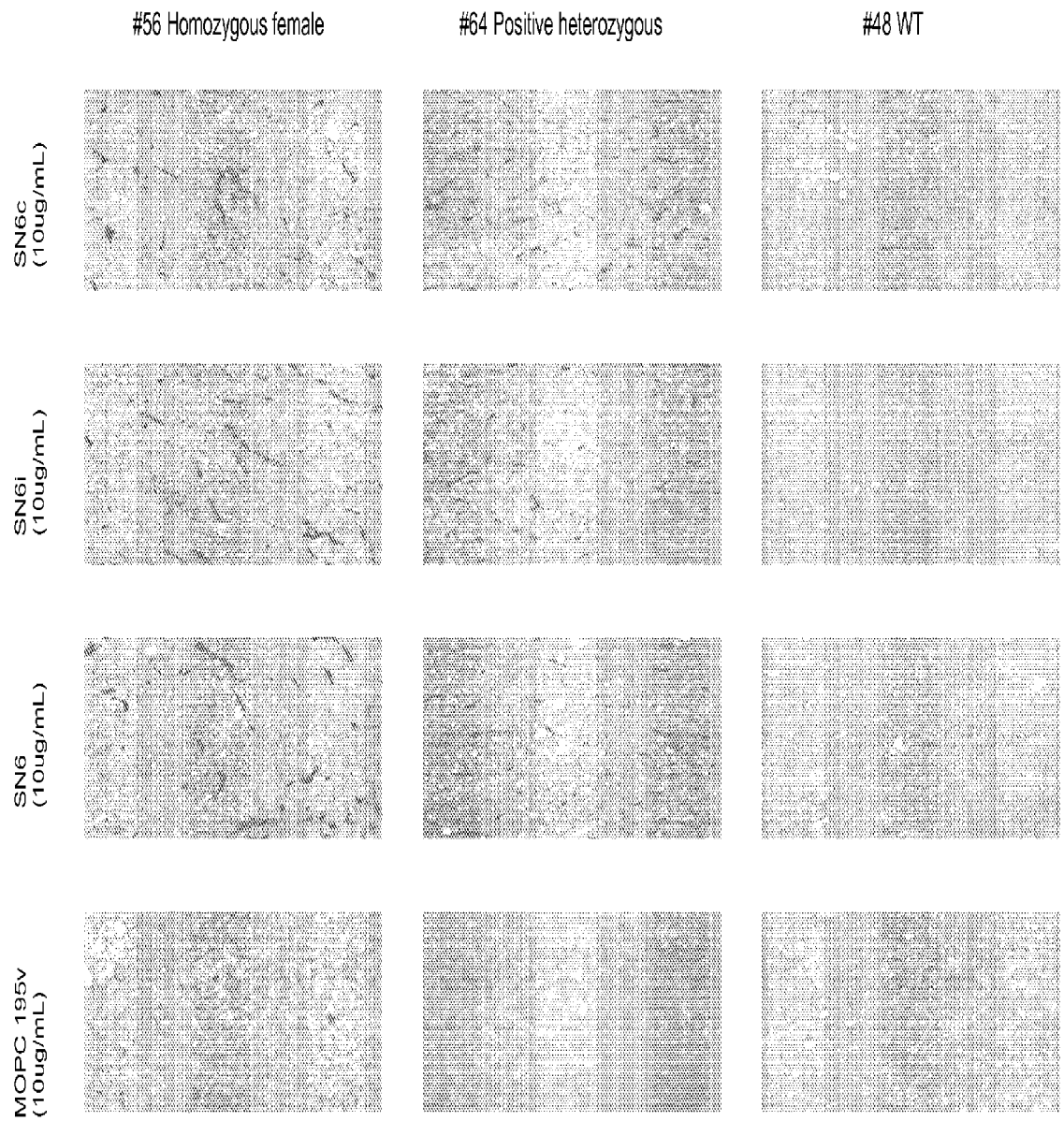

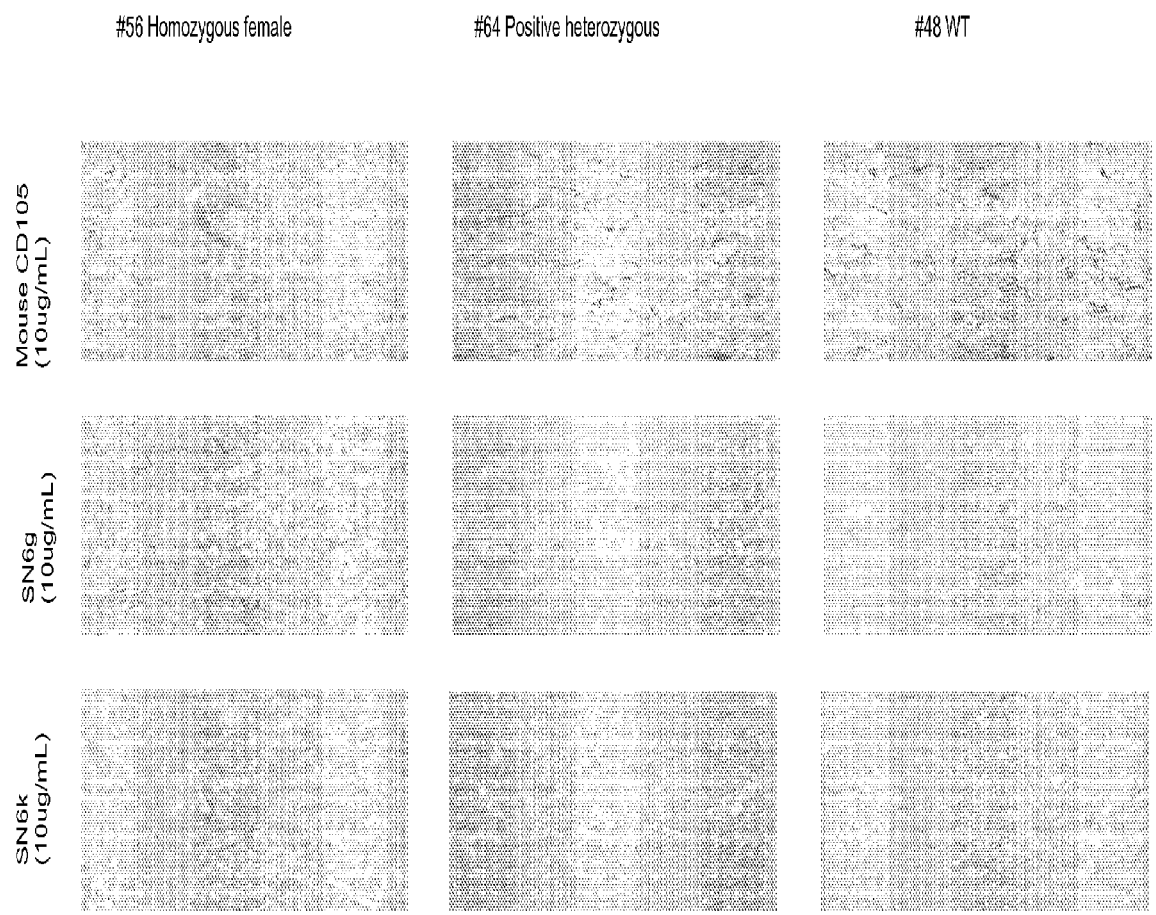

Figure 12

Sequences of PCR primers used to synthesize ENG fragments

| Primer* | Sequence |
|---|---|
| FW1 | 5'-AGA GGA ACC ATG GAA ACA GTC CAT TGT GAC CTT CAG CCT GTG GGC-3' |
| FW2 | 5'-AGA GGA ACC ATG GGT GGT AGG CTG CAG ACC TCA CCC GCA CCG ATC-3' |
| RV1 | 5'-TCC CGT CGA CTA TTA CAA GTG CAG TGG GAT TCC CAG GGC CTG GAG-3' |
| RV2 | 5'-TCC CGT CGA CTA TTA CCC GGC CGA GTG GCC CGG CAG GAC CCT CAG-3' |
| RV3 | 5'-TCC CGT CGA CTA TTA TTC TCC AGT GGT CCA GAT CTG CAT GTT GTG-3' |
| RV4 | 5'-TCC CGT CGA CTA TTA GGG TGA GGT CTG CAG CCT ACC ACC GCA GCT-3' |
| RV5 | 5'-TCC CGT CGA CTA TTA GAA AGA GAG GCT GTC CAT GTT GAG GCA GTG-3' |
| RV6 | 5'-TCC CGT CGA CTA TTA GCC TTT GCT TGT GCA ACC AGA CAG GTC AGG GCT-3' |

\* Positions of these primers are shown in Figure 10

FW1 is SEQ ID NO:1; FW2 is SEQ ID NO:2; RV1 is SEQ ID NO:3; RV2 is SEQ ID NO:4;
RV3 is SEQ ID NO:5; RV4 is is SEQ ID NO:6; RV5 is SEQ ID NO:7; is SEQ ID NO:9

Figure 13A

Amino acid sequence of knocked-in human endoglin (Plan A; exon 4 to 8).

```
  1 NSSLVTPQEP PGVNTTELPS FPKTQILEWA AERGPITSAA ELNDPQSILL    SEQ ID NO:9
 51 RLGQAQGSLS FCMLEASQDM GRTLEWRPRT PALVRGCHLE GVAGHKEAHI
101 LRVLPGHSAG PRTVTVKVEL SCAPGDLDAV LILQGPPYVS WLIDANHNMQ
151 IWTTGEYSFK IFPEKNIRGF KLPDTPQGLL GEARMLNASI VASFVELPLA
201 SIVSLHASSC GGRLQTSPAP IQTTPPKDTC SPELLMSLIQ TKCADDAMTL
251 VLKKELVA

Amino acid sequence of knocked-in human endoglin (Plan B; exon 5 and 6).

1 AQGSLSFCML EASQDMGRTL EWRPRTPALV RGCHLEGVAS HKEAHILRVL    SEQ ID NO:10
 51 PGHSAGPRTV TVRVELSCAP GDLDAVLILQ GPPYVSWLID ANHNMQIW
```

Figure 13B

3. Nucleotide sequence of knocked-in human endoglin (Plan A; exon 4 to 8).
(each exon is underlined)

SEQ ID NO:11

```
  1 ACTGCAGATC CACCAGCCAG CATTCTGGC TCCGGCTCT TTCTCTCAGC

51 CAATGGGCTG ACTCCACAAA TTACTTCCTG ACTCCTACA TGGGATAGAG

101 AGGGCACACG GCCAGGAACA GCATGCTGAG CCTCCACATG TCTCCCCAGA
                                                      Exon4
151 ATCCAGCCT GGTCACCTTC CAAGAGCCT CTGGGCTAA CACCACGGAG

201 CTGCCATCCT TCCCTAAGAC CTGAATCCTT GAGTGGGCAG CTGAGAGGAG

251 CCCCTACGC TCTGCTCTG AGCAGAAGA CCCCAGAGC ATCCTGCTGC

301 GACTGGGCA AGTCAGTTT CCCCAACAAC CTCTCTGGGC TCATGATACT

351 GTCCAGGAGG AATCTGACT CCTCTTGGCCT ACACCTCAAA CTTGGGCACC

401 AAGAGTGCAG GAGGGGACAC GCTGTGCCCC AGTTCACATG CCACAACCTA

451 GTGCTGCCTT GCTACACTGA TGCTTCTCT ACCAAATATC AGATTGAAGC

501 ATGTGGAATA TGCCAGGTTC TGACCTAAAA CCCCAGCATT TTCATACGAT

551 CTATTGTGCA TCTACTATGT GCCAAAGCCC TATCATGCTA GGCACTTGGG

601 GACACACTCA GGCCTGCCT TCCGGAGCT GATACTGTGA TGAGGGAGGT

651 GACAATAAAC ATGTACATGT ACACGATAA ATCTATATT TGGGTCTTG

701 CTGGGTGGTT TCGGCTGC AGCCTAACG GGTCATGGG CTCATCCTT

751 AGTTAACAC ACGGAGGCCC GGGGACTTGC ACAGGTCAC TTGCCAGTG

801 AGGGTGGAA GGGAAGTTCG AAACTAAGTC CTCTGACGCC TCTCCCCTC

851 TGCAGGACCG TCTGCCTGC CCCACCACTA TCTTGGCTG TGGGTGAGG

901 CGGGGTCTG TTAGGTGCAG GGCTGCTGAG GGAAGGGACT GAGGTGCCTG

951 TGTCTGTGCA GCCAAGGGT CACGATCTT CTGGATGCTG GAGGCAGC
                       Exon5
```

1001 AGGACHTGGG CGGCACGTC GAGTGGGTG CGGGTACTCC AGGATGGTC

1051 CGGGGTGCT ACTGGAGG CGTGGTCGGC CACAAGGAGG CGGCCATCCT

1101 GAAGGTCTG CCGGGCCACT CGGCCGGGTA TGGCTCTCGC CCGGCCCTG

1151 ACACTAGTCC CTACCCCGAG AGACCACCCC CCTGACCCCC CCGGCCGCT

1201 CTCCGTCCC TTATAAAGCC CCACCCTAGT CCCAGCCCA GCCCGCCGC

1251 AGCCCTGTGA GAGCACAGTC GCTTTCTCCT ACTCTAGGCT ACGCCCCTA

1301 TGGGCCCTT CCCTTTGGGC ACAAGCCTGG CCCCAGTCCC ATCCCTATCC

1351 CACAAACCCA CACCTGGCCA GGTAAGAGTG CAGCCGCCGC CTACCCGACG

1401 CCAGGCCTCG CTCCCCGCCT GGCCTGTCCG CTTCAGTGTT CCATCCGCGT

1451 CTGTCTCCCC GCAGGCCCG GAGGGTGAAG GTGAAGTGA AACTGAGGTG
                         Exon6
1501 GGCACCCGGG GATCTGATG CCGTCGTCAT CGTGCAGGGT CCGGGCTACA

1551 TGTCCAGGGT CATCGACCCC AACCACAACA TGCAGACTG GGTCAGTGGT

1601 GGGCAGTCC CGGGACACAA AACCCAAACT CCCAACCTCT GGATCAGGA

1651 AGTTCCCTGG AAAGGTGAAC CCCGAGCTG AGCTGAAGGA CAAATCACCT

1701 ATGCCCATAC GTGAGGGAAG GGGCCAGGTA GAAGACGCAG CAGGAGTGGG

1751 GACACAGCAG GACCGAGCCC TGGCATGACC CTGGCTGGCC TGCTGTGGCA

1801 CAGACTGTGT CCATGGCCCC CTGTCTGCC TCTCTCCCA CCATTAGAAT
                                                        Exon7
1851 ACTGGAGAAT ACTCCTTCAA GATCTTTCA GAGAAAACA TTGGTGGCTT

1901 CAAGCTCCCA GACACACCTC AAGGCTCCT GGTGAAGCC CGGAATCTCA

1951 ATGCAGGAT ACATGATCC TTGGTGAAT TACCCGTGT CAGCTTGTC

Figure 13B, continued

```
2001 TCACTTCATG CCTCCAGCTG CGGTGAGCAC CCTTCCCCTG CCCCTCCCTT

2051 CCCTTCCCCT CCCTTGGATC AGTGGCCACA CTGTTGGTGA AGCACCTCTG

2101 TGTGAGCTTG GGCAAGGTAC ATCAGCCTCT CTGAGCCTCA TTTTCTCAT

2151 CTGCACATGG GAACAATGGG AGTAGCTAAT CATAGAAGAG CCTGAGAATC

2201 GCTTGAACCT GGGAGATGGA GGTTGCAGTG AGCCAAGATC GTGCCACTGC

2251 ACTCCAGCCC GGGTAACAGA GCAAABCTCC GTCTCAAAA AAAAAAAAA

2301 AAAAAAAAG CCTGGTGCGG GCACACAGTG ATCACACAGT GACCAGCCGC

2351 CTGGCCTGCC TCTGCTACCC CACAGGTGGT AGGCTGCAGA CCTCACCCGC
                                     Exon8
2401 ACTGATGGAG ACCACTCCTC CCAGGACAC TTGTAGCCCG GAGCTGCTCA

2451 TGTCCTTGAT CCAGACAAAG TGTGCCGACG ACGCCATGAC CCTGGTACTA

2501 AAGAAAGAGC TTGTTGCGGT AAGGGAACTC CTGCCCCTCT GGCTCAGGAT

2551 GACATGGACA TCTGGTTCCT CCCCTAGCCC AAGACTCTTG GGGTCCTAGC

2601 CCAGGCAGGG GGCAAGTCA CGTCCCTCTG CAAGCCTTAG TTTTCCCACT

2651 TGTATAATGG AATTGATAA
```

ANTI-ENDOGLIN ANTIBODIES AND KNOCKIN MICE EXPRESSING NOVEL HUMAN/MOUSE CHIMERIC ENDOGLIN

CROSS-REFERENCE TO RELATED APPLICATIONS

This application claims priority to U.S. provisional application No. 61/445,971, filed Feb. 23, 2011, and to U.S. provisional application No. 61/445,970, filed Feb. 23, 2011, the disclosures of each of which are incorporated herein by reference.

STATEMENT REGARDING FEDERALLY SPONSORED RESEARCH OR DEVELOPMENT

This invention was made with government support under DAMD17-03-1-0463 awarded by U.S. Army Medical Research and Materiel Command. The government has certain rights in the invention.

FIELD OF THE INVENTION

The present invention is related generally to the field of cancer therapy and more specifically to compositions and methods for use in anticancer and antiangiogenic therapies.

BACKGROUND OF THE INVENTION

There is an ongoing need for compositions and methods that relate to prophylaxis and therapy of diseases that involve undesirable angiogenesis. Angiogenesis is in part related to expression of endoglin on endothelial cells.

Endoglin

Endoglin is a homodimeric tumor-associated cell membrane antigen with molecular size of 160 kilodaltons (kD) or 170 kD that is mainly expressed on leukemia cells and endothelial cells (Haruta and Seon, 1986, Proc. Natl. Acad. Sci. USA 83: 7898-7902; Gougos and Letarte, 1988, J. Immunol. 141: 1925-1933; Seon et al., 1997, Clin. Cancer Res. 3: 1031-1044). Endoglin's expression on endothelial cells is upregulated on proliferating endothelial cells of the tumor-associated vascular and lymphatic endothelium (Seon et al., Supra; Burrows et al., 1995, Clin. Cancer Res. 1: 1623-1634; Matsuno et al., 1999, Clin Cancer Res. 5: 371-382; Clasper et al., 2008, 68: 7293-7303). Endoglin is essential for angiogenesis/vascular development (Li et al., 1999, Science 284: 1534-1537; Arthur et al., 2000, Dev. Biol. 217: 42-53) and a co-receptor of TGF-β (Cheifetz et al., 1992, J. Biol. Chem. 267: 19027-19030).

Murine endoglin has been characterized as a dimer with molecular size of approximately 180 kilodaltons (kD). Human endoglin exists in two forms; i.e., a smaller 160 kD form and a larger 170 kD form with the difference between the two being found in the cytoplasmic portion of the protein. Endoglin has an extracellular region, a hydrophobic transmembrane region, and a cytoplasmic tail. A comparison of the nucleotide sequence of human endoglin with murine endoglin reveals an identity of about 71 to 72% (St. Jacques et al., 1994, Endocrinol. 134:2645-2657; Ge and Butcher, 1994, Gene 158:2645-2657). However, in the human and murine sequences encoding the transmembrane regions and cytoplasmic regions of endoglin, there is a 93-95% identity. Thus, in the human and murine sequences encoding the extracellular region to which antibody would be directed at the cell surface, there is significantly less identity than 70%. Although the amino acid sequence similarity between human and mouse endoglins appears substantial, the observed amino acid sequence differences in the extracellular regions should be sufficient for generating distinct antigenic epitopes unique to human endoglin or to mouse endoglin. This is because in peptide epitopes, even a subtle variation in the amino acid sequence comprising the epitopes or in the flanking amino acid sequences can markedly influence the immunogenicity of the epitopes (see, e.g., Vijayakrishnan et al., 1997, J. Immunol. 159:1809-1819). For instance, single amino acid substitutions in a peptide can cause marked changes in the immunogenicity of the peptide (Vijayakrishnan et al., 1997, supra). Such changes in a peptide epitope strongly influence the specificity of mAbs because mAbs define fine specificity.

Monoclonal Antibodies (mAbs) to Endoglin

SN6 is an antibody generated from immunization of mice with tumor-associated components of glycoprotein mixtures of cell membranes of human leukemia cells (Haruta and Seon, 1986, Proc. Natl. Acad. Sci. 83:7898-7902). It is a murine mAb that recognizes human endoglin. mAb 44G4 is an antibody generated from immunization of mice with whole cell suspensions of human pre-B leukemia cells (Gougos and Letarte, 1988, J. Immunol. 141:1925-1933; 1990, J. Biol. Chem. 265:8361-8364). It is a murine mAb that recognizes human endoglin. mAb MJ7/18 is an antibody generated from immunization of rats with inflamed mouse skins (Ge and Butcher, 1994, supra). It is a mAb that recognizes murine endoglin. mAb Tec-11 is an antibody generated from immunization of mice with human umbilical vein endothelial cells (Burrows et al., 1995, Clin. Cancer Res. 1:1623-1634). It is a murine mAb with reactivity restricted to human endoglin.

By the use of anti-endoglin antibodies and various staining procedures it has been determined that endoglin is expressed at moderate levels on human tumor cells such as from human leukemia, including non-T-cell-type (non-T) acute lymphoblastic leukemia (ALL), myelo-monocytic leukemia. In addition, it has been determined that endoglin is expressed at moderate to high levels in endothelial cells contained in tumor-associated vasculatures from human solid tumors, including angiosarcoma, breast carcinoma, cecum carcinoma, colon carcinoma, Hodgkins lymphoma, lymphoma, lung carcinoma, melanoma, osteosarcoma, ovarian carcinoma, parotid tumor, pharyngeal carcinoma, rectosigmoid carcinoma; and human vasculature from placenta. A lesser degree (weak) endothelial cell staining for endoglin has been observed in a variety of normal human adult tissue sections from spleen, thymus, kidney, lung and liver.

Increased endoglin expression on vascular endothelial cells has also been reported in pathological conditions involving angiogenesis. Such angiogenesis-associated diseases include most types of human solid tumors, rheumatoid arthritis, stomach ulcers, and chronic inflammatory skin lesions (e.g., psoriasis, dermatitis; Westphal et al., 1993, J. Invest. Dermatol. 100:27-34).

Angiogenesis

Angiogenesis includes the formation of new capillary blood vessels leading to neovascularization. Angiogenesis is a complex process which involves a series of sequential steps, including endothelial cell-mediated degradation of vascular basement membrane and interstitial matrices, migration of endothelial cells, proliferation of endothelial cells, and formation of capillary loops by endothelial cells. Solid tumors are angiogenesis-dependent; i.e., as a small solid tumor reaches a critical diameter, for further growth it needs to elicit an angiogenic response in the surrounding normal tissue. The resultant neovascularization of the tumor is associated with more rapid growth, and local invasion. Further, an increase in angiogenesis is associated with an increased risk of metastasis. Therefore, antiangiogenic therapy to inhibit tumor angiogenesis would suppress or arrest tumor growth and its spread.

In normal physiological processes such as wound healing, angiogenesis is turned off once the process is completed. In contrast, tumor angiogenesis is not self-limiting. Further, in certain pathological (and nonmalignant) processes, angiogenesis is abnormally prolonged. Such angiogenesis-associated diseases include diabetic retinopathy, chronic inflammatory diseases including rheumatoid arthritis, dermatitis, and psoriasis.

Antiangiogenic Therapy and Vascular Targeting Therapy of Human Solid Tumors

The progressive growth of solid tumors beyond clinically occult sizes (e.g., a few $mm^3$) requires the continuous formation of new blood vessels, a process known as tumor angiogenesis. Tumor growth and metastasis are angiogenesis-dependent. A tumor must continuously stimulate the growth of new capillary blood vessels to deliver nutrients and oxygen for the tumor itself to grow. Therefore, either prevention of tumor angiogenesis (antiangiogenic therapy) or selective destruction of tumor's existing blood vessels (vascular targeting therapy) present a strategy directed to preventing or treating solid tumors.

Since a local network of new capillary blood vessels provide routes through which the primary tumor may metastasize to other parts of the body, antiangiogenic therapy should be important in preventing establishment of small solid tumors or in preventing metastasis (See, e.g., Folkman, 1995, Nature Medicine, 1:27-31). On the other hand, the vascular targeting therapy which attacks the existing vasculature is likely to be most effective on large tumors where the vasculature is already compromised (See, e.g., Bicknell and Harris, 1992, Semin. Cancer Biol. 3:399-407). Appropriately selected monoclonal antibodies can target vascular endothelial cells of tumors and can inhibit tumor growth and/or destroy tumors by several mechanisms that include antibody-dependent cell-mediated cytotoxicity (ADCC) and induction of apoptosis (Seon et al., 2011, Current Drug Delivery 8:135-143). In another case, monoclonal antibodies and fragments thereof can be used as a means of delivering to either existing tumor vasculature or newly forming tumor neovascularization therapeutic compounds in a method of antiangiogenic therapy and vascular targeting therapy (collectively referred to as "antiangiogenic therapy"). However, there remains a need for tools that can be used in identifying monoclonal antibodies that are likely to have effective clinical applications in humans, and there is accordingly a need for such antibodies themselves.

Mouse Models for Angiogenesis-Associated Diseases

The use of mouse models of angiogenesis has been accepted and validated for the evaluation of therapeutic agents because the models have been shown to reflect the clinical parameters characteristic of the respective disease, as well as predictive of the effectiveness of therapeutic agents in patients. These mouse models include, but are not limited to: mouse model for retinal neovascularization (Pierce et al., 1995, Proc. Natl. Acad. Sci. USA 92:905-909); mouse models for rheumatoid arthritis (MRL-lpr/lpr mouse model, Folliard et al., 1992, Agents Actions 36:127-135; mev mouse, Kovarik et al., 1994, J. Autoimmun 7:575-88); mouse models for angiogenesis (Majewski et al., 1994, Int. J. Cancer 57:81-85; Andrade et al., 1992, Int. J. EXp. Pathol., 73:503-13; Sunderkotter et al., 1991, Am. J. Pathol. 138:931-939); mouse model for dermatitis (Maguire et al., 1982, J. Invest. Dermatol. 79:147-152); and mouse model for psoriasis (Blandon et al., 1985, Arch. Dermatol. Res. 277:121-125; Nagano et al., 1990, Arch. Dermatol. Res. 282:459-462). Several anti-human endoglin (hENG) monoclonal antibodies (mAbs) are known to be potentially useful for antiangiogenic therapy. These mAbs include K4-2C10 (or termed SN6f), D4-2G10 (or termed SN6a), Y4-2F1 (or termed SN6j) and P3-2G8 (or termed SN6k). However, all of these mAbs cross-react with murine endoglin or murine endothelial cells. However, these cross-reactivities are weak and evaluation of these mAbs in animal (mice) for antiangiogenic activity can be done only under limited conditions (Seon et al., 2011). Therefore, there is a need for new animal models expressing human endoglin that can be targeted by more anti-human endoglin mAbs, as well as a need for new effective anti-human endoglin mAbs themselves. The present invention meets these and other needs.

SUMMARY OF THE INVENTION

The present invention provides compositions and methods that relate to prophylaxis and therapy of angiogenesis associated disease. The invention includes providing novel knockin mice which express novel human/mouse chimeric endoglin. The mice are useful for evaluation of the in vivo efficacy of anti-human endoglin mAbs which can be used in antiangiogenic therapy of human tumor angiogenesis and human angiogenesis-associated diseases characterized at least in part by excessive vascularization. In various embodiments, the endoglin gene of the knockin mice comprise exons 4, 5, 6, 7, and 8, and combinations thereof, of the human endoglin (hENG) gene. Vectors suitable for use in homologous recombination to create the transgenic mice are provided, as are murine embryonic stem cells which comprise the knockin human endoglin gene regions.

The present invention also provides anti-endoglin mAbs which can be used as antiangiogenic agents for prophylaxis or therapy of human tumor angiogenesis and human angiogenesis-associated diseases having excessive vascularization. In various embodiments, the mAbs do not cross react with murine endoglin, and are specific for a region of human endoglin encoded by any of human endoglin exons 4, 5, 6, 7, and 8. In one embodiment, the selected mAbs are specific for the region of human endoglin encoded by human endoglin exons 4-8. Thus, the mAbs can bind with specificity to the portion of hENG which comprises hENG amino acids from Asn 121-Ala 378, inclusive.

The invention also provides methods for using the anti-endoglin mAbs for prophylaxis or therapy of human tumor angiogenesis and for angiogenesis-associated diseases having excessive vascularization. In general, the method comprise administering to an individual in need of an anti-angiogenic agent a composition comprising one or more of the mAbs, or hENG binding fragments thereof, or immunoconjugates developed from the mAbs. For each therapeutic use, the invention includes combination therapies using the mAbs, hENG binding fragments thereof, immunoconjugates, and other therapeutic agents.

BRIEF DESCRIPTION OF FIGURES

FIGS. 4A and 4B depict immunohistochemical (IHC) staining of the human/mouse chimeric ENG in 4T1 mouse breast tumors from homozygous (#56) and heterozygous (hemizygous; #64) mice. As a control, mouse ENG in 4T1 tumors from wild type mice was also stained. In FIGS. 4A and 4B, we show test results of four anti-hENG mAbs SN6h, SN6j, SN6d and SN6f as well as those of two controls which are an isotype-matched control IgG (MOPC 195v; IgG1-κ) and rat anti-mouse ENG mAb MJ7/18 (BD Bioscience). All of SN6h, SN6j, SN6d and SN6f react well with the chimeric ENG in both homozygous and heterozygous (hemizygous) mice. The isotype-matched control IgG shows no significant reactivity with either chimeric or wild type ENG. Anti-mouse ENG mAb shows no reaction with the chimeric ENG in the homozygous mice but strongly reacted with mouse ENG in the heterozygous and wild type mice. A similar IHC staining pattern of these mAbs and control IgG was observed in different homozygous (#63, #67 and #74) and heterozygous (#54 and #70) mice Similar IHC staining of the human/mouse chimeric ENG by these mAbs and control IgG was also detected in Col 26 colon tumors from homozygous (#57) and heterozygous (#81) mice.

FIGS. 5A and 5B depict IHC staining of the human/mouse chimeric ENG in 4T1 tumors by five additional anti-hENG mAbs SN6c, SN6i, SN6, SN6g and SN6k that are not shown in FIGS. 4A and 4B. SN6c, SN6i and SN6 react well with the human/mouse chimeric ENG in both homozygous and heterozygous mice. SN6g that appears to define a carbohydrate epitope reacts weakly with the chimeric ENG in the tumor of the homozygous mouse but not of the heterozygous mouse. The reactivity patterns of the isotype-matched control IgG MOPC 195v and anti-mouse ENG (CD105) mAb in FIGS. 5A and 5B are consistent with those in FIGS. 4A and 4B. MOPC 195v shows no significant reactivity with either chimeric ENG or mouse ENG. Anti-mouse ENG (CD105) mAb reacts well with mouse ENG in the 4T1 tumors of heterozygous and wild type mice, but did not react with the chimeric ENG in the tumor of homozygous mouse.

FIG. 12. Sequences of PCR Primers used to synthesize endoglin (ENG) fragments that are described in FIG. 10. The SEQ ID for each primer is provided in the figure.

FIG. 13A Amino acid sequence of knockin human endoglin (exons 4 to 8; upper panel). The amino-terminal amino acid residue N1 in exon 4 in this figure corresponds to N121 of the entire hENG molecule including the leader sequence Amino acid sequence of knockin human endoglin (exons 5 and 6; lower panel.) The amino-terminal amino acid residue A1 in exon 5 in this figure corresponds to A175 of the entire hENG molecule including the leader sequence. SEQ ID for each exon set is provided.

FIG. 13B. Nucleotide sequence of human endoglin gene including exons 4-8; exon sequences are underlined). The SEQ ID is as provided.

DETAILED DESCRIPTION OF THE INVENTION

Figure 1:
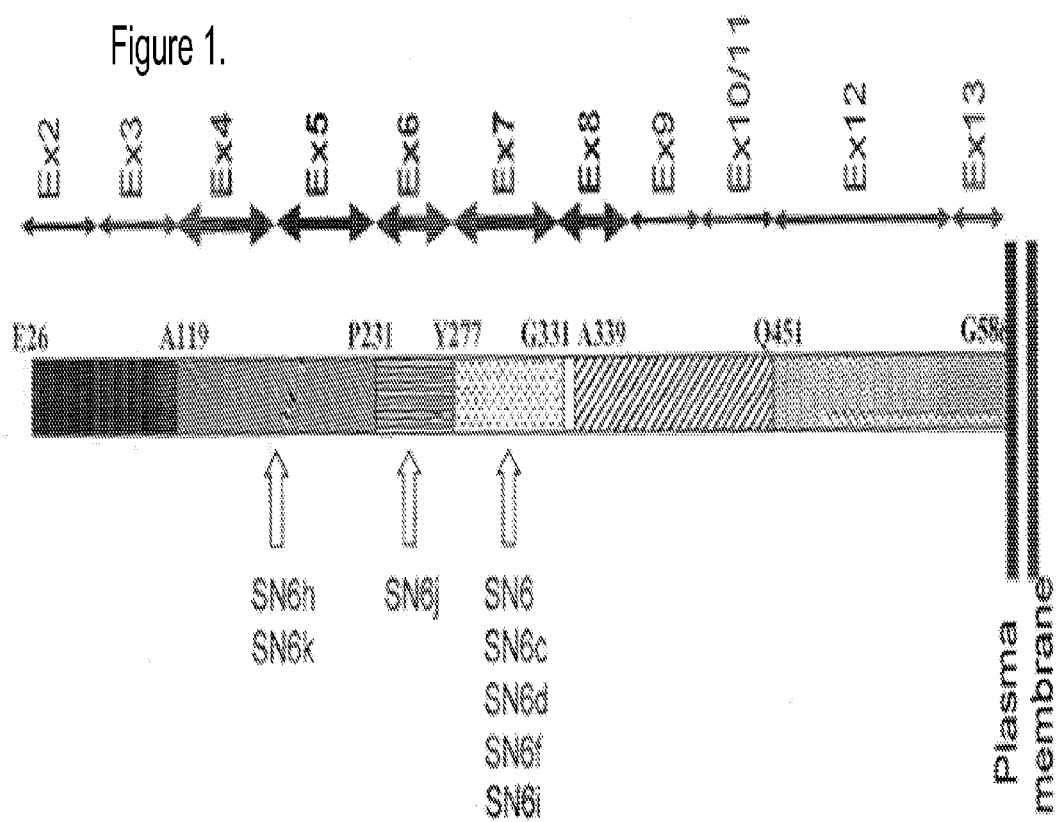
FIG. 1 is a graphic description of linear sequence epitopes of human endoglin (hENG) defined by eight anti-hENG mAbs that were generated in our laboratory. Molecular map of hENG epitopes defined by SN6 series anti-hENG mAbs and the corresponding exons. The amino-terminal amino acid residue of each of the seven polypeptide fragments is shown. The amino-terminal residue of the mature translated hENG as well as the fragment 1 is Glu26 as shown. The map was constructed based on the reactivities of the 12 anti-hENG mAbs with eight bacterially expressed recombinant hENG polypeptide fragments including a fragment that consists of the entire extracellular domain of hENG (see FIG. 10). SN6 series mAbs relevant are shown in this figure. The epitope defined by SN6k is a putative conformational epitope. All 12 anti-hENG mAbs developed to date by us define extracellular epitopes. The corresponding exons of human ENG gene are shown in the figure. Exon 4 to Exon 8 that are shown in bold letters were used to replace the corresponding exons of mouse ENG gene in generation of the knockin mice in Plan A which is described further below. Figure hatching and amino acid numbering denotes peptides that were synthesized for epitope mapping studies.

The present invention relates to compositions and methods for prophylaxis and/or therapy for angiogenesis-associated conditions.

In one aspect, the invention provides compositions which comprise antibodies that are specific for certain portions of human endoglin, and wherein the antibodies do not cross react with murine endoglin expressed by murine epithelial cells. Fragments of the antibodies which are likewise specific for certain portions of human endoglin but do not cross react with endoglin expressed by murine epithelial cells are also provided.

In another aspect, the invention provides compositions suitable for making transgenic mice. The compositions include vectors that are suitable for use in homologous recombination such that transgenic mice which express chimeric endoglin can be made. In particular embodiments, the vectors are adapted for homologous replacement of exons 4, 5, 6, 7, and 8, or combinations thereof, of the murine endoglin gene with the homologous exons from the human endoglin gene.

In another aspect of the invention, methods for prophylaxis and/or therapy of conditions associated with undesirable angiogenesis are provided. The methods comprise administering to an individual in need of anti-angiogenic therapy a monoclonal antibody or a human endoglin (hENG) binding fragment thereof. Various modifications to the antibodies and the hENG binding fragments thereof can be made and are discussed further below. Methods for therapy of angiogenesis related disorders include combinations therapies which include use of the presently provided mAbs and/or hENG binding fragments thereof.

The term "angiogenesis-associated disease" or "angiogenesis-associated condition" is used hereinto mean certain pathological processes in humans where angiogenesis is abnormally prolonged. Such angiogenesis-associated diseases include but are not necessarily limited to diabetic retinopathy, adult macular degeneration, chronic inflammatory diseases, rheumatoid arthritis, dermatitis; psoriasis, stomach ulcers, and most types of human solid tumors.

The term "angiogenesis inhibitor" is used herein to mean a composition of matter including, but not necessarily limited to peptides, proteins, enzymes, polysaccharides, oligonucleotides, DNA, RNA, recombinant vectors, and drugs which function to inhibit angiogenesis. Angiogenesis inhibitors are known in the art. Representative examples include natural and synthetic biomolecules such as sunitinib, sorafenib, bevacizumab (avastin), paclitaxel, 0-(chloroacetyl-carbomyl) fumagillol ("TNP-470" or "AGM 1470"), thrombospondin-1, thrombo-spondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b]quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid.

The term "antiangiogenic therapy" is used herein to mean therapy targeted to vasculature which comprises cells that express endoglin. Endoglin is expressed at higher levels on proliferating vasculature as compared to quiescent vasculature. Therapeutic approaches provided by the invention can be directed against angiogenesis (i.e., the formation of new capillary blood vessels leading to neovascularization), and/or against existing vasculature and relating to a disease condition (e.g., vascular targeting therapy).

The term "antibody fragment" or "fragment thereof" is used hereinto mean a portion or fragment of an intact antibody molecule, wherein the fragment retains antigen-binding function; i.e., F(ab')2, Fab', Fab, Fv, single chain Fv ("scFv"), Fd' and Fd fragments. Methods for producing the various fragments from rnAbs are well known to those skilled in the art (see, e.g., Pluckthurn, 1992, Immunol. Rev. 130:152-188).

The term "imunoconjugate" is used herein to mean a conjugate comprised of the anti-endoglin mAbs or a fragment thereof according to the present invention (or alternatively, an anti-endoglin mAb, or fragment thereof, that recognizes human vascular endothelial cells but lacks crossreactivity with mouse endoglin) and at least one antitumor agent or at least one angiogenesis-inhibitor. Such antitumor agents are known in the art and include, but not limited to, toxins, drugs, enzymes, cytokines, radionuclides, photodynamic agents, and angiogenesis inhibitors. Toxins include ricin A chain, mutant *Pseudomonas* exotoxins, diphtheria toxoid, streptonigrin, boamycin, saporin, gelonin, and pokeweed antiviral protein. Drugs include daunorubicin, methotrexate, Capecitabine, paclitaxel and calicheamicins. Radionuclides include radiometals. Cytokines include transforming growth factor (TGF)-β, interleukins, interferons, and tumor necrosis factors. Photodynamic agents include porphyrins and their derivatives. The methods for complexing the anti-endoglin mAbs or a fragment thereof with at least one antitumor agent are well known to those skilled in the art (i.e., antibody conjugates as reviewed by Ghetie et al., 1994, Pharmacal. Ther. 63:209-34). Often such methods utilize one of several available heterobifunctional reagents used for coupling or linking molecules.

The term "isotype control immunoglobulin" is used herein, for purposes of the specification and claims, to mean a species specific (e.g. raised in the same species as the antibody to which it is compared), isotype-matched (e.g., of the same immunoglobulin (Ig) class and subclass as the antibody to which it is compared) Ig which does not bind with specificity to the antigen to which the compared antibody has binding specificity, as will be more apparent from the following embodiments.

The term "tumor" is used herein, to mean a tumor expressing endoglin at moderate to high levels (as compared to expression by normal tissue of the same type) such as human leukemias, including non-T-cell-type (non-T) acute lymphoblastic leukemia (ALL), myelo-monocytic leukemia; and human solid tumors, with its surrounding vasculature expressing endoglin at moderate to high levels (as compared to expression by normal tissue of the same type) including angiosarcoma, breast carcinoma, cecum carcinoma, colon carcinoma, Hodgkins lymphoma, lymphoma, lung carcinoma, melanoma, osteosarcoma, ovarian carcinoma, parotid tumor, pharyngeal carcinoma, prostate carcinoma, and rectosigmoid carcinoma.

A drawback to conventional chemotherapy and radiotherapy is the lack of selectively delivering the therapy to its intended target, diseased tissue, rather than to normal tissue. Monoclonal antibodies have been used to deliver therapeutics with greater target specificity, thereby reducing toxicity. Murine mAbs or fragments thereof have been used to treat human disease after the major part of a mAb or a fragment was replaced with the corresponding human component by humanization or chimerization.

Antiangiogenic therapy may overcome some of the major problems associated with conventional chemotherapy or immunotherapy of human solid tumors. First, antiangiogenic therapy may allow circumvention of the problem of acquired drug resistance. Drug-resistant tumor mutants are easily generated because of the genetic instability of tumor cells. However, genetically-stable normal cells, such as vascular endothelial cells, would be far less adept at generating drug resistance. Additionally, antiangiogenic therapy may overcome the problem of tumor heterogeneity for the reasons as discussed above. Further, physiologic bathers for high molecular weight drugs (such as mAbs and immunoconjugates) to penetrate into solid tumors will be circumvented by targeting a tumor's vasculature rather than tumor cells. This is because the therapeutic agent delivered in antiangiogenic therapy selectively acts on the vascular endothelial cells lining the blood vessels of the tumor rather than the tumor cells themselves (although a delivered therapeutic agent may secondarily act on tumor cells with which it comes in contact). Vascular endothelial cells are directly accessible to circulating high molecular weight drugs/antitumor agents. Furthermore, destruction of all tumor-associated blood vessels is not necessary for effective antiangiogenic therapy. This is because large numbers of tumor cells are critically dependent upon a small number of capillary endothelial cells. If a capillary bed is damaged as a result of antiangiogenic therapy, a significant number of tumor cells will die of nutrient and oxygen deprivation. An additional advantage is that a single type of therapeutic agent developed for antiangiogenic therapy may be applied to many types of solid tumors and angiogenesis-associated diseases. The invention includes the following approaches to providing new and improved compositions and methods for prophylaxis and/or therapy of angiogenesis associated diseases.

Compositions for Making Transgenic Mice

Compositions and methods for making homologous replacements of genes (i.e., gene knockins) in mice are well known in the art. The present invention provides vectors suitable for creating murine embryonic stem cells (ES) which comprise hENG coding sequences. The transgenic ES can be used for making knockin mice which express chimeric murine/human endoglin and are accordingly valuable for studying the effects of antiangiognic agents, including but not necessarily limited to the mAbs and hENG binding fragments thereof provided by the invention.

Figure 2:
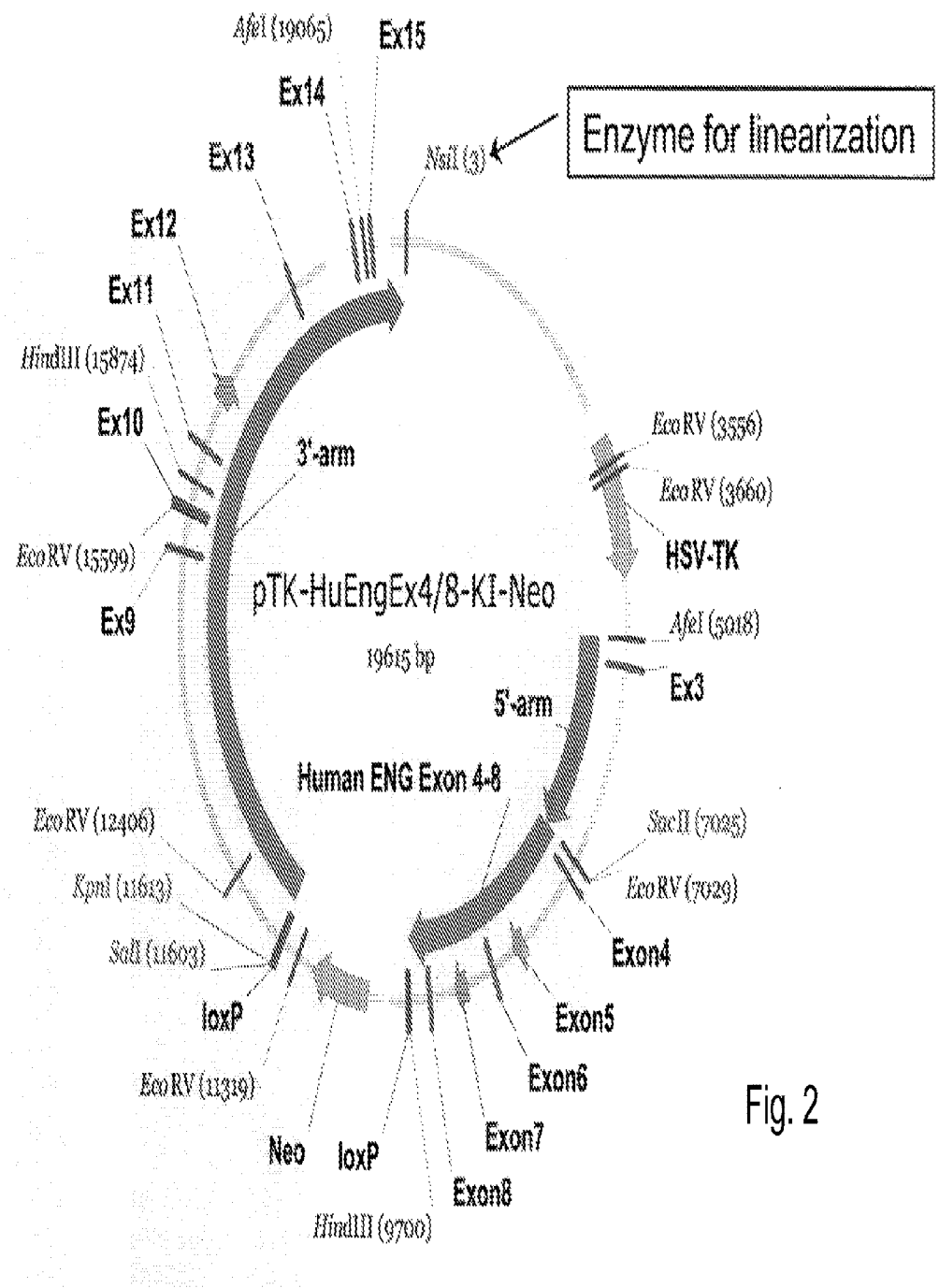
FIG. 2 depicts the hENG exons 4-8 knockin vector. hENG exons 4-8 were derived from human male BAC library RPCI-11. The 5'-arm and 3'-arm were derived from BALB/cByJ BAC library CHORI-28.

In one embodiment, the invention provides a vector for use in replacement of a portion of the murine endoglin gene with a portion of the hENG gene. As such, the vector is adapted to facilitate homologous recombination with the murine endoglin gene. In general, a vector that is adapted for use in homologous combination with a target site in a recipient chromosome will have features known to those skilled in the art. These features include but are not necessarily limited to a selectable marker, such as the well characterized Neo marker, polycloning sites into which the replacement gene segment is cloned as well as for inserting gene segments that are the same as those in the targeted portion of the chromosome so that the replacement is targeted correctly, a site for linearization of the vector, sites which are recognized by enzymes involved in certain recombination events, such as LoxP sites, and promoter sequences. A representative knockin vector that is suitable for inserting hENG exons 4, 5, 6, 7 and 8 into a murine chromosome is depicted in FIG. 2. The sequences of the amino acids encoded by exons 4-8 of the hENG gene are presented in FIG. 13A, while the sequences of the exons themselves and intervening human introns are depicted in FIG. 13B, wherein the exon sequences are underlined. The amino-terminal amino acid residue N1 in FIG. 13A (upper panel sequence) is Asn at position 121 of the full-length hENG amino acid sequence, including the leader sequence, while the carboxy-terminal amino acid in FIG. 13A (upper panel) is Ala at position 378 of the full-length hENG amino acid sequence, including its leader sequence.

Thus, in various embodiments, the invention provides a recombinant vector that is suitable for replacing a portion of the murine endoglin gene with a homologous portion of the human endoglin gene. In particular embodiments, the vector is configured such that each of exon 4, 5, 6, 7 and 8 can been replaced by human endoglin gene exons 4, 5, 6, 7 and 8, respectively. In other embodiments, the vector is adapted so that any one, two, or three, four or five of the murine exons can be replaced by the homologous human exons. In one embodiment, the vector is configured to replace only exons 5-6 of the murine endoglin by human exons 5-6.

Those skilled in the art will recognize that the sequence of the human endoglin exons in the vectors used to create transgenic ES and/or a transgenic mouse according to the invention can be identical to endogenous human endoglin exon sequences. However, due to the redundancy in the genetic code, the human endoglin exons can be different from endogenous human endoglin sequences, and can comprise any nucleotide sequences that encode the portion of the human endoglin protein that is encoded by human endoglin exons 4-8, and all combinations of those exons. It is expected that significant variability in intron sequences in the knockin vector relative to the murine intron sequences would be tolerated, since the intron sequences are not protein coding. In certain cases, it is desirable that intron sequences in the knockin vector are substantially the same length as intronic sequence in the murine endoglin gene.

In order to use the vectors of invention, in general, ES can be obtained using routine techniques and are chosen for their ability to integrate into and become part of the germ line of a developing embryo so as to create germ line transmission of the transgene. Thus, any ES cell or cell line that can do so is suitable for use in the invention. Introduction of a knockin vector described herein into ES cells may be accomplished using a variety of methods well-known in the art, including, for example, electroporation, microinjection, and calcium phosphate treatment. For introduction of the chosen DNA sequence, the knockin vector is added to the ES cells under appropriate conditions for the insertion method chosen. For example, if the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockin construct. Screening for cells which contain the transgene (e.g., homologous recombinants) may be done using a variety of methods, such as by screening with specific probes or by polymerase chain reaction (PCR), or by Southern blotting. Once selected, ES cells are injected into a blastocyst of an animal (e.g., a mouse) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knockin" animal. Progeny harboring the homologously recombined DNA in their germ cells can be identified by standard techniques and used to breed animals in which all cells of the animal contain the homologously recombined DNA.

Mice and Embryonic Stem Cells

By using the compositions and methods described above, or any other suitable techniques, the invention provides transgenic murine ES knockin mice stably expressing novel human/mouse chimeric endoglin. We developed two chimeric ENG genes which are described in what are referred to herein as "Plan A" and "Plan B."

In Plan A, a chimeric ENG gene comprising hENG exons 4-8 was designed and constructed so that the translated chimeric protein could be targeted by several (7 or 8) of the 12 anti-hENG mAbs that we have developed. In Plan B, we generated a smaller chimeric gene comprising hENG exons 5-6 encoding a protein that was expected to be targeted by a few (2 or 3) of the 12 mAbs we have generated in connection with this invention. We carried out Plan B considering the possibility that a chimeric ENG containing a large hENG protein (containing a dimer of 258 amino acids-polypeptides and carbohydrates) in Plan A may not function well in mice and may induce defective vascular development in the mice. It should be noted that mice lacking ENG die from defective vascular development (Li et al., 1999, Science 284: 1534-1537) and mutations of hENG in human are associated with hereditary hemorrhagic telangiectasia type 1 (HHT 1; McAllister et al., 1994, Nature Genetics 8: 345-351). However, we found that knockin mice generated using both Plans A and B develop normally and do not show any signs of hemorrhagic telangiectasia-like symptoms. These results indicate that the chimeric ENGs are physiologically functional in mice.

An important next question was whether the translated human/mouse chimeric ENG protein is effectively expressed in angiogenic blood vessels. We addressed this question by immunohistochemical (IHC) staining of tumor tissues from the knockin mice. Microvessels of tumors (colon26 and 4T1) in Plan A mice reacted strongly with 7 anti-hENG mAbs (SN6, SN6c, SN6d, SN6f, SN6h, SN6i and SN6j) and weakly with 1 anti-hENG mAb (SN6g) in IHC staining. The results indicate that tumors in the Plan A knockin mice may be targeted by each of the 7 or 8 anti-hENG mAbs. Plan A and Plan B mice are useful for screening a wide variety of anti-hENG agents. For example, Plan A knockin mice are useful for screening for the best or best two of the 8 reactive anti-hENG mAbs with regard to their in vivo antitumor efficacy. It is important to note that the hENG part of the Plan A chimeric ENG contains immunodominant epitopes to which many anti-hENG mAbs are directed. Therefore, the Plan A knockin mice are valuable for evaluating the in vivo antitumor efficacy of many anti-hENG mAbs or other anti-hENG agents. Furthermore, the knock-in mice are valuable for finding appropriate combinations of an anti-hENG mAb with other therapeutic agents to potentiate antitumor efficacy of the mAb and hENG binding fragments thereof. It is believed that the present invention is the first disclosure of knockin mice stably expressing human/mouse chimeric ENG and anti-ENG mAbs/immunoconjugates that recognize only the hENG part of the chimeric ENG and show antiangiogenic activity in antiangiogenic therapy.

Antibodies

Another embodiment of the present invention provides anti-hENG mAbs. The antibodies can be characterized by their binding specificity for epitopes expressed on the hENG part of the human/mouse chimeric ENG in knockin mice, which is restricted to certain tumor vasculature and proliferating vascular endothelial cells, as characteristic of angiogenesis. These mAbs are evaluated for in vivo efficacy in the mouse model to perform the studies necessary to evaluate clinical efficacy, pharmacokinetics, and potential adverse side effects of antiangiogenic therapy in humans. Eight such anti-endoglin mAbs were tested in this invention: mAb SN6 from hybridoma clone N13A1, SN6c from clone L41C8, SN6d from clone D31A2, SN6f from K42C10, SN6g from clone 112G6, SN6h from clone G42C2, SN6i from clone K21C7 and SN6j from clone Y42F1. Properties of these mAbs are described in FIG. 1, FIG. 8, FIG. 9 and Table 1.

It will be apparent from the foregoing description and the Examples and Figures presented herein that the invention provides in various embodiments anti-hENG mAbs which can be used as antiangiogenic agents for prophylaxis or therapy of human tumor angiogenesis and human angiogenesis-associated diseases which are characterized at least in part by excessive vascularization. Examples of such angiogenesis-associated diseases include but are not necessarily limited to all human solid tumors, as well as diabetic retinopathy, age-related macular degeneration, chronic inflammatory diseases including rheumatoid arthritis, dermatitis, and psoriasis.

In various embodiments, the mAbs and hENG binding fragments thereof do not cross react with murine endoglin. The mAbs can be specific for a region of human endoglin encoded by any of human endoglin exons 4, 5, 6, 7, and 8. Representative exon sequences and amino acid sequences encoded by them are depicted in FIGS. 13A and 13B. In various embodiments, the mAbs are specific for the region of human endoglin encoded by human endoglin exon 4-8 and accordingly can bind with specificity to the portion of hENG which comprises or consists of hENG amino acids from N121-A378, inclusive. Exemplary antibodies with these characteristics are also depicted graphically in FIG. 1. The invention does not include the mAbs designated SN6f and SN6j, which crossreact with murine endoglin. The hybridomas K42C10 and Y42F1 which produce SN6f and SN6j, respectively which were deposited with the American Type Culture Collection and were accorded deposit number HB-12172 and HB-12171, respectively. In one embodiment, the antibodies provided for use in antiangiogenic and antitumor treatment comprise SN6c, SN6d, SN6i, and combinations thereof. Hybrodomas producing each of the mAbs described herein are encompassed within the invention.

Figure 8:
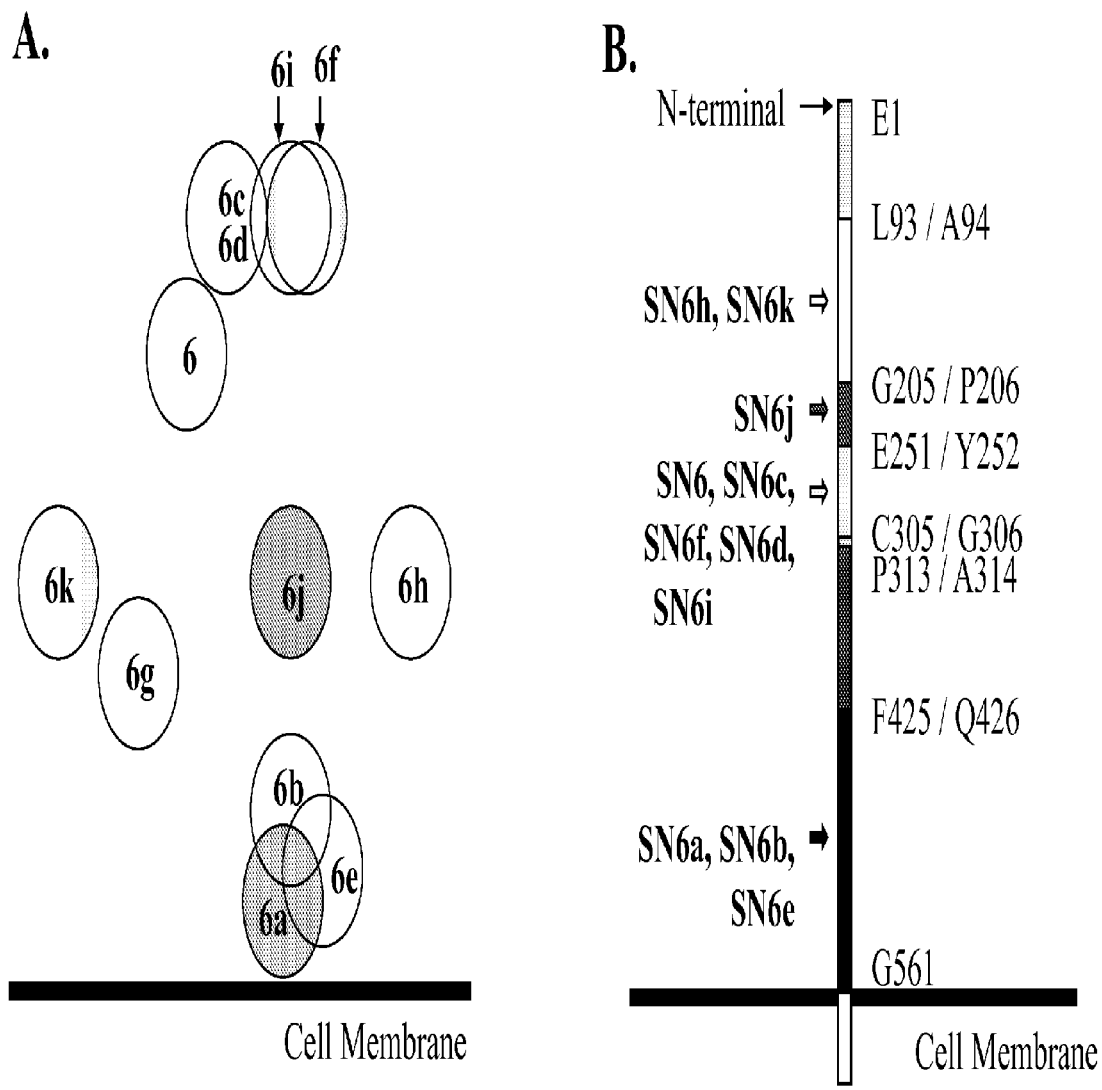
FIG. 8 provides a graphical description of results obtained by antibody analysis to determine steric epitopes of endoglin recognized by the antibodies of the invention.
Figure 9:
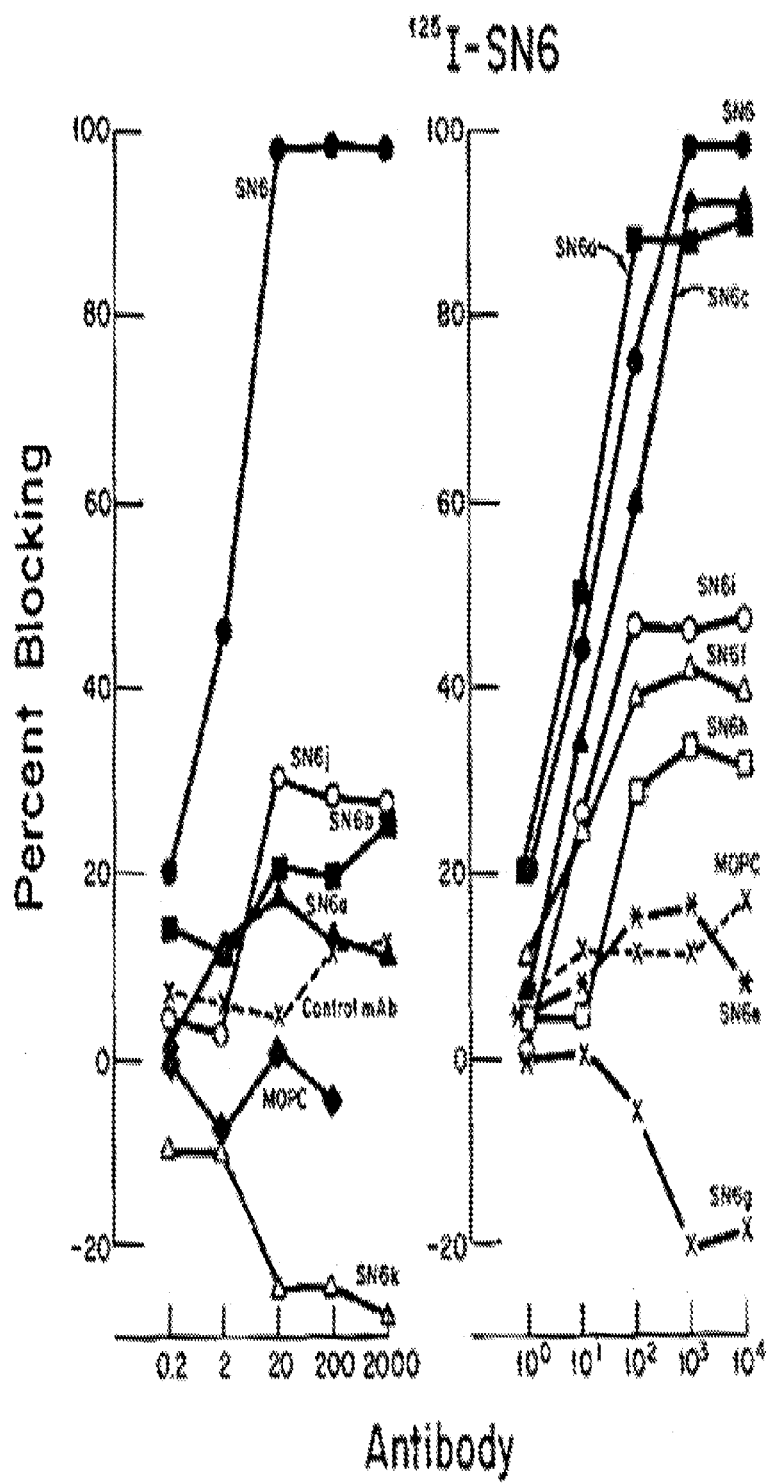
FIG. 9 provides a graphical depiction of results obtained from competitive antibody binding between SN6 series anti-endoglin monoclonal antibodies (mAbs) and $^{125}$I-labeled SN6 as measured by a cellular radioimmunoassay.
Figure 10:
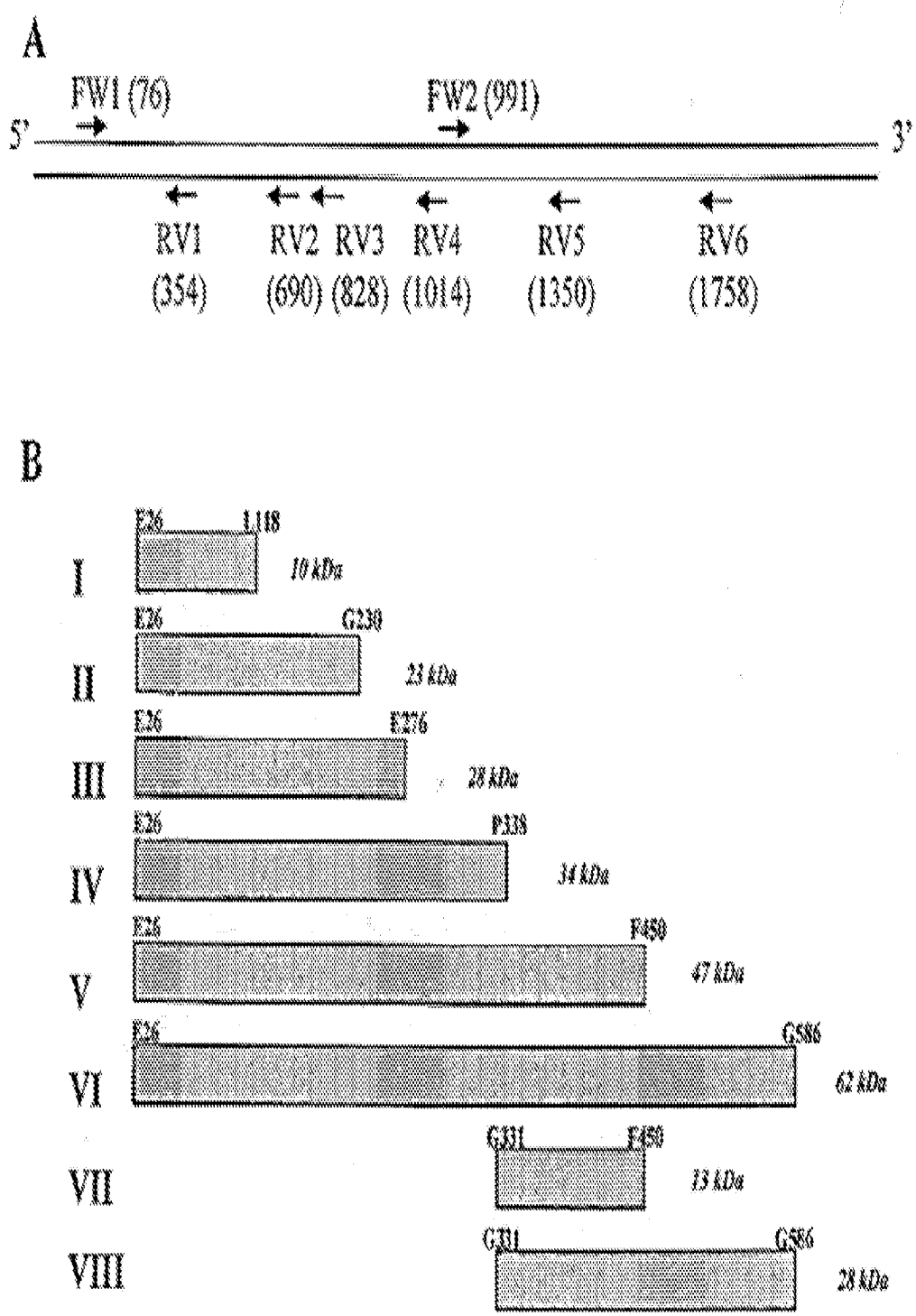
FIG. 10 depicts oligonucleotide primers of cDNA encoding S-ENG (A) and bacterially expressed recombinant ENG fragments (B). Oligonucleotide primers were used in PCR to synthesize DNA fragments encoding different portions of the extracellular domain of ENG protein molecule. Numbers in the parentheses following the primer names in panel A are the positions from 5' ends. Forward direction primer FW1 was combined with reverse direction primers RV1, RV2, RV3, RV4, RV5 and RV6, respectively, in the PCR to synthesize DNA encoding ENG fragments I, II, III, IV, V and VI in panel B. Forward direction primer FW2 was combined with reverse direction primers RV5 and RV6, respectively, to synthesize DNA encoding ENG fragments VII and VIII. Fragment VI corresponds to the full-length extracellular domain while other fragments correspond to different portions of ENG molecule.
Figure 11:
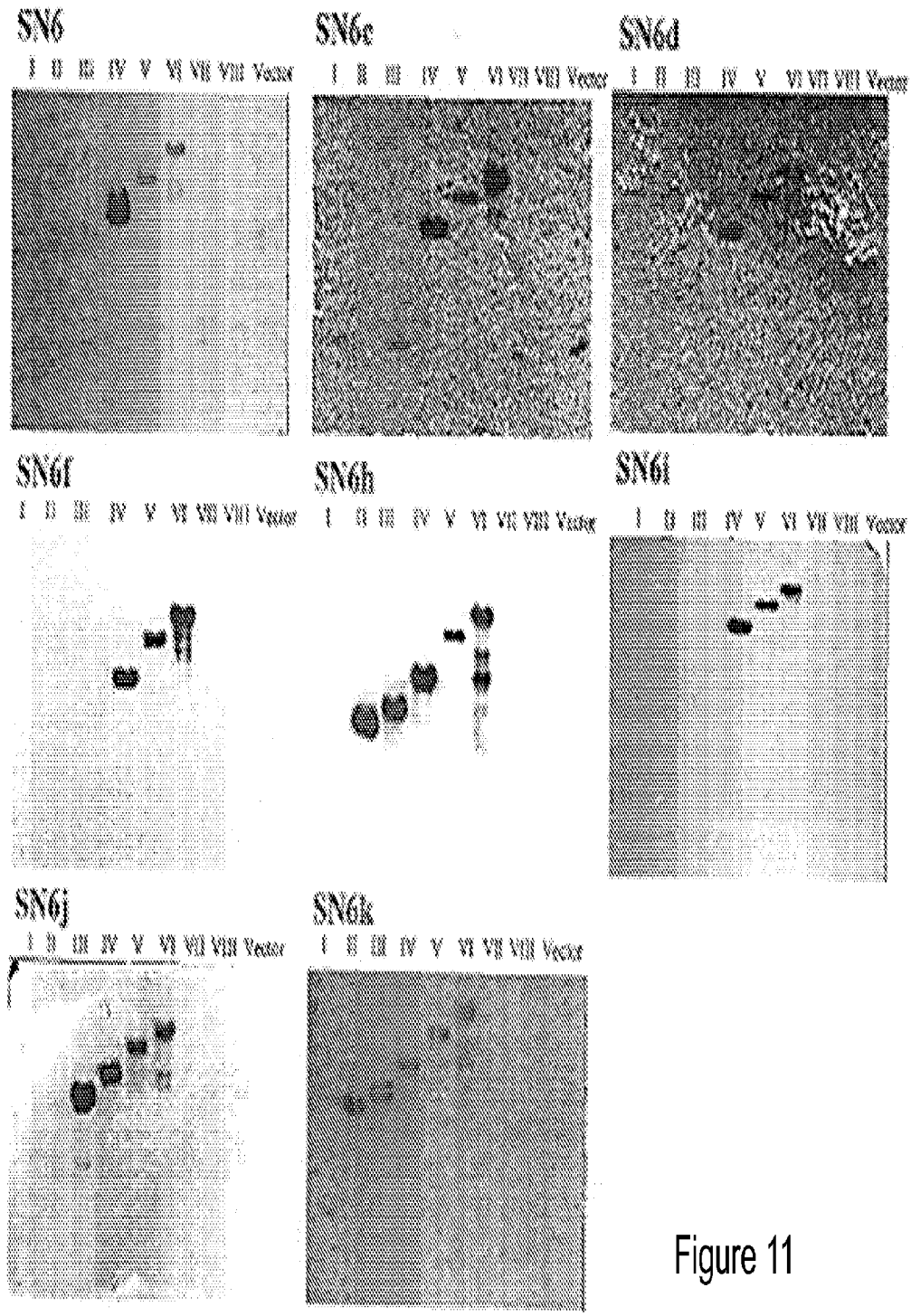
FIG. 11. Depicts western blots of recombinant ENG fragments using anti-ENG mAbs. Inclusion bodies harvested from the IPTG-induced *E. coli* BL21 (DE3), which had been transfected with blank plasmid vector pET-21d (+) or plasmid vectors pET-21d (+) containing cDNA encoding each of the eight ENG fragments (i.e., I to VIII), were dissolved in a buffer containing 8 M urea. The dissolved polypeptide fragments were fractionated on 15% gels in SDS-PAGE under the reducing conditions. The separated ENG fragments were detected in Western blot using each of the 12 anti-ENG mAbs. In addition, the dissolved recombinant fragments were subjected to SDS-PAGE under the non-reducing conditions and reactivities of the separated fragments with SN6a, SN6g and SN6k were detected in Western blot. Under the reducing conditions, distinct reactive bands were detected with SN6, SN6b, SN6c, SN6d, SN6e, SN6f, SN6h, SN6I and SN6j, but not with any of SN6a, SN6g and SN6k. However, SN6a and SN6k reacted with distinct ENG fragments under the non-reducing conditions. Results of SN6a, SN6b and SN6k are not shown here because they are not relevant to this patent application. SN6g which defines an epitope containing sialic acid(s) did not react with any of the bacterially expressed recombinant ENG fragments under either reducing or non-reducing conditions. The experiments were repeated and similar results were observed.

Characterizations of specific examples of antibodies of the invention are presented in FIGS. 8 and 9. In particular, in FIG. 8, Panel A presents a steric epitope map of ENG that is defined by twelve SN6 series anti-ENG mAbs. This map was constructed by performing three different tests that include 1) a sequential competitive inhibition test using several $^{125}$I-labeled SN6 series mAbs, 2) a simultaneous competitive binding assay, and 3) a comparison of the degree of susceptibility of individual epitopes to various enzymatic digestions. Panel B presents a linear sequence epitope map of ENG showing location of epitopes defined by eleven SN6 series mAbs (excluding SN6g) Amino-terminal and/or carboxy-terminal amino acid residue of each peptide fragment used for the epitope mapping are indicated in this figure Amino acid residues in this figure are numbered excluding the leader sequence of 25 amino acids. Therefore, the amino-terminal amino acid is designated as E1 (Glu 1) instead of E26.

FIG. 9 provides results from competitive antibody binding experiments between SN6 series anti-endoglin mAbs and $^{125}$I-labeled SN6 as measured using cellular radioimmunoassay. One of the tests that was performed to compare the steric location of individual epitopes defined by individual SN6 series anti-endoglin mAbs was a competitive binding assay and the results of it are shown in FIG. 9, where the abscissa for the left panel is ng of the purified mAbs (SN6, SN6a, SN6b, SN6j and SN6k), control mAb (SN4d; IgG2a-κ) and control mouse IgG (MOPC 195variant; IgG1-κ). The abscissa for the right panel is relative concentration derived from the reciprocals of 10-fold serial dilutions of ascites fluids of SN6 series hybridomas (SN6, SN6c, SN6d, SN6e, SN6f, SN6g, SN6h and SN6i) and MOPC 195 variant plasmacytoma. The target antigen was endoglin (CD105) on KM-3 leukemia cells. In this test, endoglin-expressing KM-3 (an immature B-lineage leukemia cell line) cells were first incubated with different concentrations of individual SN6 series mAbs and control mouse IgG/or control mAb, and subsequently $^{125}$I-labeled SN6 mAb was allowed to react with the preincubated KM-3 cells. Preinculation of KM-3 cells with SN6 (autologous mAb; a positive control) blocked the subsequent binding of $^{125}$-SN6 almost completely at the maximum while similar preincubation of KM-3 cells with SN6c or SN6d blocked the subsequent binding of $^{125}$I-SN6 by approximately 90% at the maximum. On the other hand, preincubation of KM-3 cells with SN6i or SN6f blocked subsequent binding of $^{125}$I-SN6 by 47% and 40%, respectively, at the maximum. Therefore, the epitopes defined by SN6c and SN6d are in different locations sterically from the epitope defined by SN6f (termed SN6f epitope). SN6i epitope is close to SN6f epitope but not identical to SN6f epitope. It is of interest that preincubation with higher concentrations of SN6g and SN6k did not block but rather enhanced the subsequent binding of $^{125}$I-SN6. This may be due to binding of SN6g and SN6k to endoglin on KM-3 cells inducing a conformational change of the endoglin molecule in such a way that the SN6 epitope becomes more exposed. It will be apparent from FIG. 9 that in certain embodiments, antibodies provided by the present invention can competitively inhibit binding of SN6 to human endoglin.

In one embodiment, the invention provides an anti-hENG mAb termed SN6c, which is generated by the hybridoma clone L41C8. This mAb defines an epitope in the region of hENG between Ile 271 and Ala 378 that is encoded by exons 7-8 of hENG gene. This mAb does not cross-react with murine endothelial cells.

In another embodiment, the invention provides anti-hENG mAb termed SN6d which is generated by the hybridoma clone D31A2. This mAb defines an epitope in the region of hENG between Ile 271 and Ala 378 that is encoded by exons 7-8 of hENG gene. This mAb does not cross-react with murine endothelial cells.

In another embodiment, the invention provides anti-hENG mAb termed SN6i which is generated by the hybridoma clone K21C7. This mAb defines an epitope in the region of hENG between Ile 271 and Ala 378 that is encoded by exons 7-8 of hENG gene. This mAb also does not cross-react with murine endothelial cells.

Also included in the invention are fragments of the antibodies that bind with specific to hENG as described herein, and which do not cross react with murine endoglin. The antibody fragments include but are not necessarily limited to Fab, Fab', (Fab')2, Fv, single chain (ScFv), diabodies, multivalent antibodies, fusion proteins comprising one or more antibody portions, and any other modified immunoglobulin molecule that comprises an antigen recognition site of desired specificity for hENG but does not cross-react with murine endoglin.

The invention also provides for chimeric and partially or fully humanized version of the antibodies disclosed herein. Methods for making human and chimeric antibodies are well known in the art. In one embodiment, a humanized antibody comprises murine hypervariable regions having endoglin binding specificity for the region of human endoglin between human endoglin amino acid N121 and amino acid A378, and constant region and variable region sequences of human immunoglobulin. In certain embodiments, the antibody is a humanized antibody comprising murine hypervariable regions having endoglin binding specificity for the region of human endoglin between human endoglin Asn 121 and Ala 378, and a constant region and variable region sequences (excluding hypervariable regions) of human immunoglobulin. In other embodiments, the antibody is a chimerized antibody comprising murine variable regions having endoglin binding specificity for the region of human endoglin between human endoglin amino Ile 217 and amino acid Ala 378, and constant regions sequences of human immunoglobulin.

The invention also provides compositions comprising the mAbs described herein, or hENG binding fragments thereof, with a pharmaceutically acceptable carrier. Such compositions for use in therapeutic purposes may be prepared by mixing the mAbs or fragments thereof with any suitable pharmaceutically acceptable carriers. Some examples of compositions suitable for mixing with the agent can be found in: *Remington: The Science and Practice of Pharmacy* (2005) 21st Edition, Philadelphia, Pa. Lippincott Williams & Wilkins.

These agents can be used alone, or in compositions also comprising other therapeutic agents, and/or in combination treatment modalities. Other therapeutic agents may include, but not limited to, doxorubicin, cyclophosphamide, paclitaxel, Capecitabine, sunitinib, sorafenib and bevacizumab (avastin).

In one embodiment, the invention provides immunoconjugates. An immunoconjugate can be formed by coupling an anti-endoglin mAb, or a fragment thereof, to at least one anti-tumor agent, wherein the resultant immunoconjugate retains its selective immunoreactivity restricted to certain tumor vasculature and proliferating vascular endothelial cells characteristic of angiogenesis. A naked anti-hENG mAb or the immunoconjugate can be administered to an individual in need of antiangiogenic therapy.

Methods

In various embodiments, any antibody, modified or otherwise, or hENG binding fragments thereof, can be tested using a mouse model described herein. This embodiment is suitable for testing a test antibody to determine whether it is a candidate for treatment of human angiogenesis related diseases. Having evaluated parameters such as clinical efficacy and pharmacokinetics in the a mouse model provided by the invention, the antiangiogenic therapy may then be "scaled up" to human treatment. A physiological basis for scaling up the therapeutic agents comprising mAbs from a mouse model to humans is known to those skilled in the art (see, e.g., Baxter et al., 1995, Cancer Res. 55:4611-4622).

Another embodiment of the present invention comprises a method for using anti-hENG mAbs, or an hENG binding fragment thereof, according to the present invention for prophylaxis and/or therapy of an angiogenesis associated disease. In this regard, the method can be used for prophylaxis and/or therapy for an individual in need of treatment. The individual in need of treatment may be diagnosed with, suspected of having, or at risk for developing an angiogenesis-associated disease. Thus, the individual may be diagnosed with, suspected of having, or at risk for developing any human solid tumors, as well as any other disease selected from the group consisting of diabetic retinopathy, age-related macular degeneration (AMD) and chronic inflammatory diseases, the latter including rheumatoid arthritis, dermatitis, and psoriasis.

It will be recognized by those of skill in the art that the form and character of the particular dosing regimen for any mAb or hENG binding fragment thereof, whether used alone, or in pharmaceutical preparations, or in combination with one or more other therapeutic agents, will be dictated at least in part by the route of administration and other well-known variables, taking into account such factors as the size, gender, health and age of the individual to be treated, and the type and stage of angiogenesis associated disease with which the individual may have or be at risk for. Based on such criteria, one skilled in the art can determine an effective amount of a composition to administer to the individual.

Compositions comprising the antibodies or hENG binding fragments thereof, in addition to other therapeutic agents if desired, can be administered to an individual using any available method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. The method of the invention can be performed prior to, concurrently, or subsequent to conventional anti-cancer therapies, including but not limited to chemotherapies, surgical interventions, and radiation therapy.

As will be clear from the foregoing description and the Examples and Figures presented herein, the presently provided anti-hENG mAbs have binding specificity for an epitope on the hENG part of the human/mouse chimeric ENG, and can be used to inhibit tumor-associated angiogenesis, and inhibit vasodilation of preexisting small blood vessels (vascular-targeting). Since it is believed the present results demonstrate that an anti-endoglin mAb, or an immunoconjugate containing the same, can effectively target tumor-associated vasculature in vivo, another embodiment of the present invention is a method of antiangiogenic therapy which utilizes any anti-endoglin mAb recognizing endoglin expressed on human vasculature endothelial cells. More particularly, because the anti-ENG mAbs of the present invention exhibit immunoreactivity to ENG and therapeutic efficacy in targeting tumor-associated vasculature in vivo, such mAbs establish reasonably predictive utility in humans for themselves and for mAbs that recognize only ENG on the surface of human vascular endothelial cells.

The following examples are presented to illustrate the present invention. They are not intended to limiting in any manner.

Example 1

This Example Development provide a description of the development of Knockin mice which stably expressing a novel human/mouse chimeric endoglin.

Twelve anti-hENG mAbs we developed define at least 8 different steric epitopes as determined by immunological and biochemical tests (e.g., competitive binding assay). The sequence epitopes, defined in a particular region in the amino acid sequence of hENG, of these mAbs were determined using recombinant polypeptide fragments corresponding to different parts of ENG molecule. FIG. 1 illustrates the sequence epitope.

Figure 3:
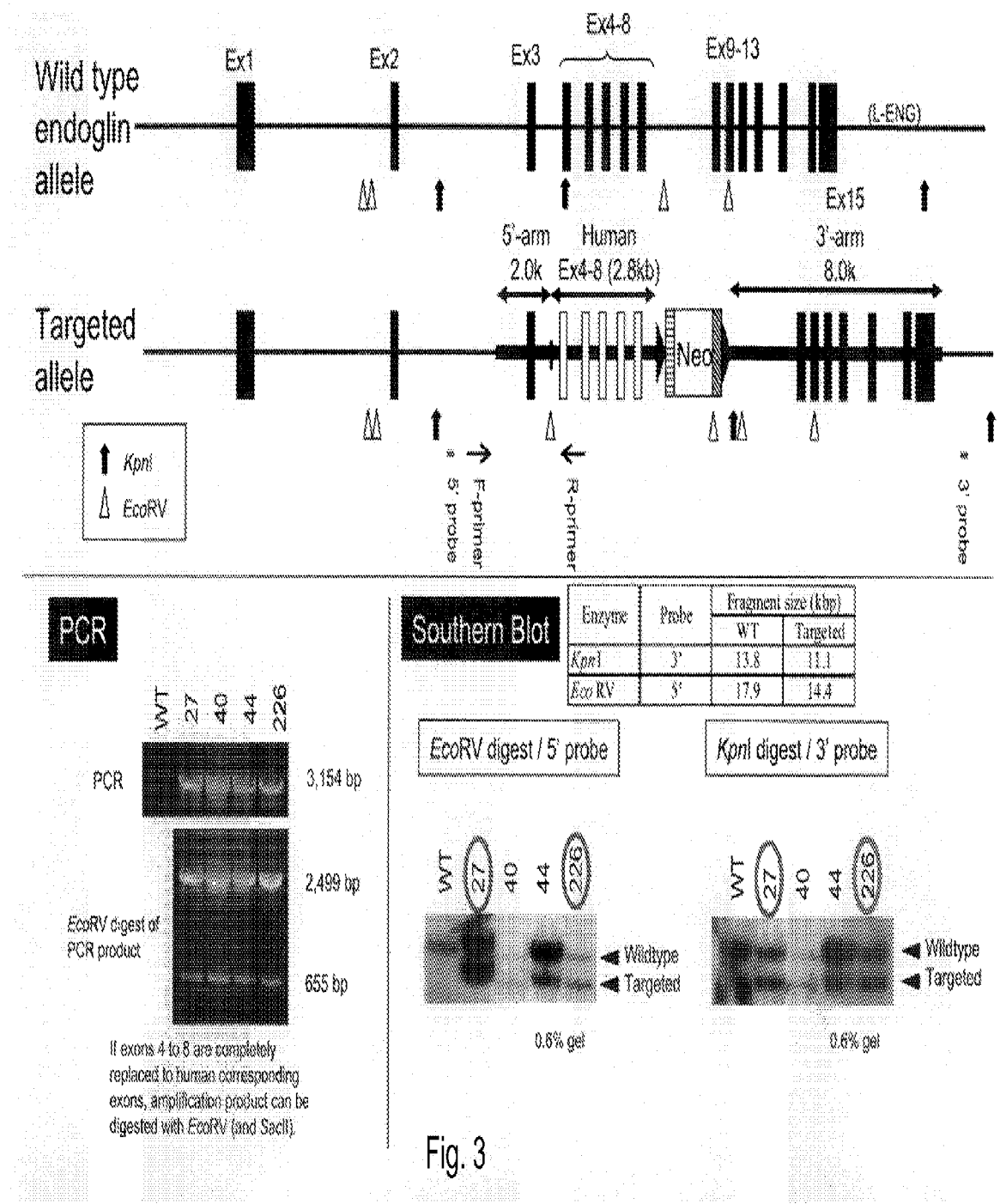
FIG. 3 depicts a mouse wild type ENG gene and the targeted ENG gene in which mouse ENG exons 4-8 were replaced with hENG exons 4-8 and shows insertion of a Neo marker. Gene targeting was performed by transfection of the gene knockin vector into mouse embryonic stem (ES) cells. The correctly targeted ES cell clones were screened by PCR and Southern blot as indicated in the figure. These assays indicated that clones 27 and 226 contain the desired targeted gene. NeoMarker was later deleted from the targeted gene by crossing a male mouse carrying the targeted gene with a Cre female mouse.

We humanized the murine ENG (mENG) region covered by exons 4-8 because this region contains epitopes defined by the majority of the anti-hENG mAbs we have produced to date. In addition, the hENG protein region encoded by Exon 7 contains immunodominant epitopes. We constructed a gene targeting vector which was used for the targeted replacement of exons 4-8 of mENG with the corresponding exons of hENG (FIG. 2). The targeted knock-in gene was examined by PCR and Southern blot. Both results confirmed that exons 4-8 in mENG were successfully replaced with hENG exons 4-8 (FIG. 3). The Neo marker in the targeted gene in the knock-in mice was removed by mating the Neo-carrying male mice with Cre-deleter female mice. After repeated mating/breeding, we obtained the desired knock-in mice that carry the human/mouse chimeric ENG gene but free of Neo and Cre genes; this was confirmed by PCR and Southern blot experiments. Using a similar strategy, (Plan B), we replaced exons 5-6 of mENG gene with the corresponding exons 5-6 of hENG gene.

We then tested whether the translated human/mouse chimeric ENG protein is effectively expressed in angiogenic blood vessels. We addressed this question by immunohistochemical (IHC) staining of tumor tissues from the knock-in mice (FIGS. 4A, 4B, FIGS. 5A and 5B). To this end, we inoculated colon26 murine colon adenocarcinoma cells or 4T1 murine breast cancer cells subcutaneously (s.c.) into the left flank of the knock-in mice and wild type mice (control). The generated tumors were removed and blood vessels in the removed tumors were examined by IHC staining with anti-hENG mAb, isotype-matched control IgG and control mAb. Both colon26 tumors and 4T1 tumors showed consistent IHC staining patterns with multiple anti-hENG mAbs. Tumors from six different knock-in mice showed consistent IHC staining patterns. In addition to SN6j, all other six anti-hENG mAbs (SN6h, SN6, SN6c, SN6d, SN6f and SN6i), whose sequential epitopes are located in the protein sequence region encoded by exons 4-8 (see FIG. 1), also showed effective immunostaining of tumor-associated blood vessels in the knock-in mice. In addition, SN6g that defines a carbohydrate epitope stained weakly. Examples of the IHC staining are shown in FIGS. 4A, 4B, 5A and 5B.

Results of the IHC study validate our experimental design. The knock-in mice develop normally and are healthy. The results indicate that the generated chimeric ENG is physiologically functional in mice.

Example 2

This Example provides a description of production of anti-anti-hENG mAbs. Anti-hENG mAb SN6 was generated by immunizing a mouse with a tumor-associated antigen-enriched fraction of cell membrane glycoproteins from ENG-expressing human leukemia cells (Haruta and Seon, 1986, Proc. Natl. Acad. Sci. USA 83: 7898-7902). The remaining seven anti-hENG mAbs of the present invention were generated by immunization of mice with a purified human endoglin (hENG) preparation. hENG was purified from human acute lymphoblastic leukemia (ALL) cells. Cell membrane glycoproteins were isolated using detergent extraction and lectin affinity chromatography as described previously (Haruta and Sean, 1986, Proc. Natl. Acad. Sci. USA, 83:7898-7902, herein incorporated by reference). The isolated glycoproteins were applied to an immunoaffinity column containing anti-endoglin mAb SN6 (Seon et al., 1997, Clin. Cancer Res. 3:1031-1044.) which had been equilibrated with 25 mM Tris-HCl, pH 8.0 containing 0.5% taurocholate, 0.15 M NaCl, 2 mM EDTA, 0.03% NaN3 and 0.5 mM phenylmethylsulfonyl fluoride. The bound materials were eluted with 50 mM diethylamine-HCl, pH 11.3 containing 0.5% taurocholate, 2 mM EDTA, 0.03% NaN3 ("alkaline buffer"). The eluate was immediately neutralized by the addition of one-tenth volume of 0.5 M Tris-HCl buffer, pH 7.1. The eluted material was reapplied to the immunoaffinity column and the bound material was eluted with the alkaline buffer further containing 0.01% cytochrome-c (a 12.4 kD carrier protein) and neutralized. The eluted material was dialyzed and concentrated using ultrafiltration (e.g., with a YM-10 membrane). This purification process was carried out at 4-6° C. Purification of hENG was monitored by a solid phase radioimmunoassay using mAb SN6, and confirmed by gel electrophoresis with silver staining. The resultant hENG preparation contained a single, major component of 170 kD under unreduced conditions, and 92 kD under reduced conditions.

In a first immunization protocol, 2 female BALB/c mice were immunized with the isolated hENG following an immunization protocol described previously (Seon et al., 1983, Proc. Natl. Acad. Sci. USA, 80:845-849) with modifications. Briefly, an antigen solution comprising 10 μg of the hENG preparation in 100 μl of 10 mM Tris-HCl buffer, pH 7.5, with 0.5% taurocholate, 0.15 M NaCl, and 14 μg cytochrome-c, was mixed with an equal volume of adjuvant (e.g., Fruend's complete) and then injected subcutaneously at multiple sites on each of the mice. In addition, $1 \times 10^9$ Bordetella pertussis bacteria in 100 μl saline were injected at different sites. Two booster immunizations of the antigen solution in adjuvant were administered subcutaneously. A last immunization comprising 40 μl antigen solution containing 8 μg hENG preparation mixed with 200 μl saline was administered intraperitoneally. The spleens were removed and fused with P3/NS1/1-Ag4-1 (NS-1) mouse myeloma cell line 4 days after the last immunization. Cell fusion, hybridoma screening, and immunoglobulin class determination were performed as described previously (Haruta and Seon, 1986, supra). In a second immunization protocol, a female BALB/c mouse was immunized with the isolated hENG as described for the first experiment, but without the administration of B. pertussis. Eleven hybridomas generated by these immunizations produce individually different anti-hENG mAbs that were further characterized.

As shown in FIGS. 4A, 4B, 5A and 5B, seven of the eleven mAbs generated using these immunization protocols demonstrated binding specificity for the hENG part of the human/mouse chimeric ENG that is stably expressed in the knockin mice.

Example 3

This Example provides a characterization of the anti-hENG mAbs. mAbs SN6f, SN6g, SN6h, SN6i and SN6j were generated using the immunization protocol first described in Example 2 whereas mAbs SN6c and SN6d were generated using the second immunization protocol. mAb SN6 was generated using a tumor-associated antigen-enriched fraction of cell membrane glycoproteins from human leukemia cells as described in Example 2. The specificity of immunoreactivity of each of these eight mAbs was characterized by testing them against various hematopoietic cell lines in a cellular radioimmunoas say (RIA) and by immunoprecipitation of hEDG using methods previously described (Haruta and Sean, 1986, supra). Briefly, 20 μl of a 1:9 dilution of the culture fluids of individual hybridomas and $2 \times 10^5$ hematopoietic cells in each test by RIA. Mouse plasmacytoma IgG1 and IgG2a were included in the assays as controls. The results indicating immunoreactivity (+) or no detectable immunoreactivity (−) are shown in Table 1.

TABLE 1

REACTIVITY OF MONOCLONAL ANTIBODIES SN6, SN6c, SN6d, SN6f, SN6g, SN6h, SN6i AND SN6j
WITH HUMAN LEUKEMIA-LYMPHOMA (HLL) AND EBV-TRANSFORMED B CELL LINES

| Cell Line | Origin of Cell Line | Reactivity | | | | | | | |
|---|---|---|---|---|---|---|---|---|---|
| | | SN6 (N13A1) | SN6c (L41C8) | SN6d (D31A2) | SN6f (K42C10) | SN6g (I12G6) | SN6h (G42C2) | SN6i (K21C7) | SN6j (Y42F1) |
| HLL non-T/non-B | | | | | | | | | |
| KM-3 | ALL* | + | + | + | + | + | + | + | + |
| NALM-16 | ALL | + | + | + | + | + | + | + | + |
| REH | ALL | + | + | + | + | + | + | + | + |
| HLL Pre-B | | | | | | | | | |
| NALM-6 | ALL | + | + | + | + | + | + | + | + |
| NALM-1 | CML-BC | + | + | + | + | + | + | + | + |
| HLL B | | | | | | | | | |
| BALL-1 | ALL | − | − | − | − | − | − | − | − |
| BALM-2 | ALL | − | − | − | − | − | − | − | − |
| Daudi | BL | − | − | − | − | − | − | − | − |
| Ramos | BL | − | − | − | − | − | − | − | − |
| U698M | LS | − | − | − | − | − | − | − | − |
| BALM-3 | LY | − | − | − | − | − | − | − | − |
| SU-DHL-4 | HL | − | − | − | − | − | − | − | − |

TABLE 1-continued

REACTIVITY OF MONOCLONAL ANTIBODIES SN6, SN6c, SN6d, SN6f, SN6g, SN6h, SN6i AND SN6j
WITH HUMAN LEUKEMIA-LYMPHOMA (HLL) AND EBV-TRANSFORMED B CELL LINES

| Cell Line | Origin of Cell Line | SN6 (N13A1) | SN6c (L41C8) | SN6d (D31A2) | SN6f (K42C10) | SN6g (I12G6) | SN6h (G42C2) | SN6i (K21C7) | SN6j (Y42F1) |
|---|---|---|---|---|---|---|---|---|---|
| HLL T | | | | | | | | | |
| MOLT-4 | ALL | − | − | − | − | − | − | − | − |
| JM | ALL | − | − | − | − | − | − | − | − |
| CCRF-CEM | ALL | − | − | − | − | − | − | − | − |
| CCRF-HSB2 | ALL | − | − | − | − | − | − | − | − |
| Ichikawa | ALL | − | − | − | − | − | − | − | − |
| HPB-MLT | ALL | − | − | − | − | − | − | − | − |
| HUT-78 | SS | − | − | − | − | − | − | − | − |
| HLL Myelomonocytic | | | | | | | | | |
| ML-2 | AML | + | + | + | + | + | + | + | + |
| HL-60 | APL | + | + | + | + | + | + | + | + |
| U937 | HL | + | + | + | + | + | + | + | + |
| EBV-transformed B | | | | | | | | | |
| CCRF-SB | | − | − | − | − | − | − | − | − |
| RPMI 8057 | | − | − | − | − | − | − | − | − |
| RPMI 1788 | | − | − | − | − | − | − | − | − |

*Abbreviations used in this table:
ALL, acute lymphoblastic leukemia;
CML-BC, chronic myelocytic leukemia in blast crisis;
BL, Burkitt's lymphoma;
LS, lymphosarcoma;
LY, lymphoma;
HL, histiocytic lymphoma;
SS, Sezary syndrome;
AML, acute myelocytic leukemia;
APL, acute promyelocytic leukemia As shown by Table 1 for the anti-endoglin mAbs of the present invention, and as previously determined for anti-hENG mAb SN6, immunoreactivity was demonstrated for the immature B-lineage leukemia cell lines tested (KM-3, REH, NALM-1, NALM-6 and NALM-16) and the myelomonocytic leukemia cell lines tested (ML-2, HL-60 and U937). However, they did not react with any of the mature B-lineage leukemia-lymphoma cell lines (BALL-1, BALM-2, BALM-3, Daudi, Ramos, U698M, and SU-DHL-4), any of the T leukemia cell lines (MOLT-4, JM, CCRF-CEM, CCRF-HSB2, Ichikawa, HPB-MLT and HUT-78), nor the EBV-transformed B cell lines (CCRF-SB, RPMI 1788 and RPMI 8057). The immunoprecipitation assay showed that all eight anti-hENG mAbs of the present invention precipitated a 170 kD component under unreduced conditions and a 92 kD component under reduced conditions.

The specificity of immunoreactivity of each of the eight mAbs SN6, SN6c, SN6d, SN6f, SN6g, SN6h, SN6i and SN6j were further characterized by using these mAbs in histochemical staining of several human malignant tissues. The tissues included malignant tissues of breast, colon, kidney, lung, and lymph node. The tissues were frozen, then air-dried and fixed with acetone, and stained according to the methods standard in the art. The immunohistochemical (IHC) staining of the malignant tissue with each of the eight mAbs showed that these mAbs reacted strongly with the vascular endothelium associated with all of the malignant tissues tested, whereas the isotype control IgG failed to demonstrate any significant staining in each tissue.

In summary, the anti-hENG mAbs according to the present invention showed strong immunoreactivity to ENG as shown by selective reactivity to ENG-expressing human leukemia-lymphoma cells and human vascular endothelial cells as demonstrated by their reactivity with malignant tumor vasculature. Since ENG is primarily a proliferation-associated marker for endothelial cells undergoing active angiogenesis, the anti-hENG mAbs according to the present invention may be used to selectively target antiangiogenic therapy to tumor vasculature or the excessive vascularization present in other angiogenesis-associated diseases in humans.

It would be preferable for any potentially new agents for antiangiogenic therapy to be evaluated for their safety and efficacy in an animal model before the agents are applied to the clinical trials involving human patients. In this regard, the developed knockin mice stably expressing human/mouse chimeric ENG and mAbs specifically reactive with the hENG part of the chimeric ENG in the knockin mice according to the present invention are valuable for evaluating safety and efficacy of these mAbs and immunoconjugates formed using these mAbs.

Figure 4B:
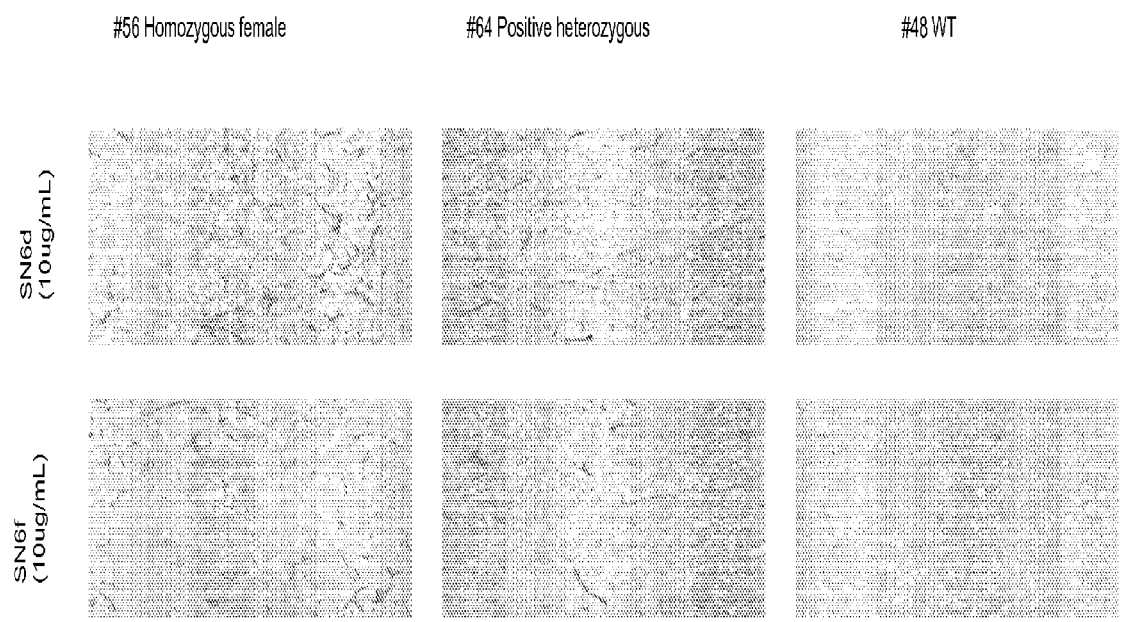

The specific reactivity of the eight anti-hENG mAbs of the present invention with the human ENG part of the human/mouse chimeric ENG in the knockin mice is shown by the IHC staining test as illustrated in FIGS. 4A, 4B, 5A and 5B. mAbs SN6h, SN6j, SN6d and SN6f showed strong IHC staining demonstrating strong reactivity with the human/mouse chimeric ENG in 4T1 tumor from the homozygous and heterozygous (hemizygous) knockin mice, but did not show significant IHC staining with mouse ENG in 4T1 tumor from wild type mice (FIGS. 4A and 4B). An anti-mouse ENG (CD105) mAb showed strong IHC staining with mouse ENG in the heterozygous and wild type mice (FIG. 4A). An isotype-matched control IgG did not show any significant IHC staining with either chimeric ENG or mouse ENG (FIG. 4A). mAbs SN6c, SN6i and SN6 showed similar IHC staining patterns to those of SN6h, SN6j, SN6d and SN6f as shown in FIG. 5A. mAb SN6g showed weak IHC staining with the chimeric ENG in the homozygous mice (FIG. 5B). mAb SN6k did not show significant IHC staining with either chimeric or mouse ENG (FIG. 5B). IHC staining patterns of anti-mouse ENG mAb and control IgG in this set of experiment are essentially same as those of the above set of experiment shown in FIG. 4A (FIGS. 5A and 5B). The mAbs, that show strong IHC staining with chimeric ENG in 4T1 breast tumor, show also strong IHC staining with chimeric ENG in Col 26 colon tumor. This finding is consistent with the previous findings that ENG expression pattern is common among angiogenic vascular of many different solid tumors (Seon et al., 2011, Curr. Drug Deliv. 8:135-143).

In summary, all eight anti-hENG mAbs in the present invention react with the human ENG part of the chimeric human/mouse chimeric ENG in the knockin mice in the present invention.

Example 4

This Example provides a description of using anti-hENG antibodies for antiangiogenic therapy. While an anti-hENG mAb may be administered by routes other than intravenously (i.v.), a preferred embodiment of the illustration is i.v. administration of the mAb. This is because it is primarily the proliferating vasculature comprising the angiogenesis that is the target of the therapy; and thus, administering the mAb i.v. saturates the targeted vasculature much quicker than if another route of administration is used. Additionally, the intravenous route allows for the possibility of further targeting to specific tissues. Thus, in a variation of this embodiment, a catheter may be used to direct the mAb to the location of the target angiogenesis. For example, if tumor angiogenesis is the target of the anti-angiogenic therapy, and if the tumor is located in the liver, then the mAb may be delivered into the hepatic portal vein using a catheter. In this variation, there is even less systemic distribution of the mAb, thereby further minimizing any potential side effects from antiangiogenic therapy.

Figure 6A:
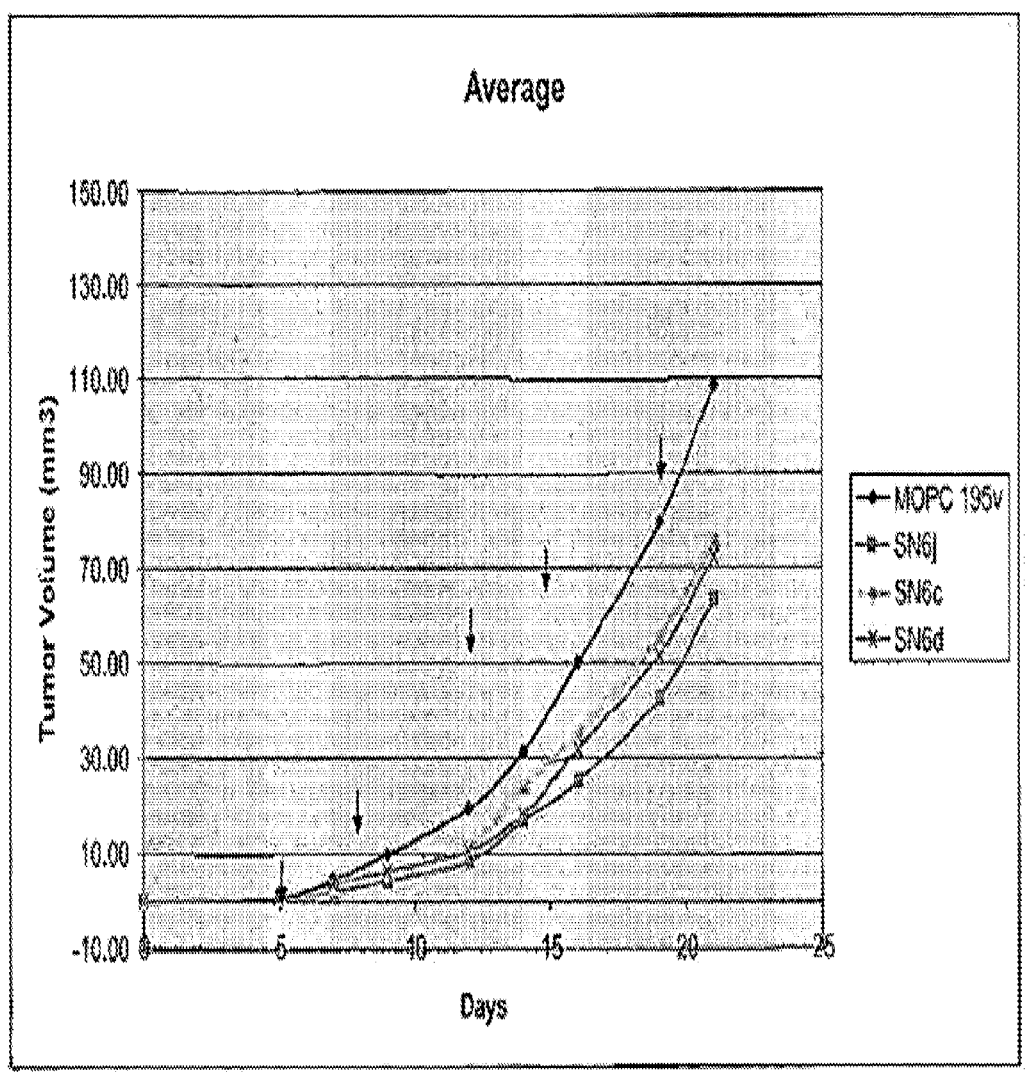
FIG. 6A depicts suppression of growth of 4T1 breast tumors in knockin mice expressing human/mouse chimeric ENG by anti-hENG mAb SN6j, SN6c or SN6d. The control is an isotype-matched control IgG MOPC 195v. Mice bearing established subcutaneous tumors of a similar size were distributed evenly into four different groups (n=7 for each group) at the onset of the therapy. Individual mice with established tumors in each group were treated by intravenous administration of 50 μg of an isotype-matched control IgG, SN6j, SN6c or SN6d. The administration was repeated at 3 or 4 days intervals (twice a week) as indicated by vertical arrows. Each graph line in the figure represents the average of tumor volumes of seven mice in each group.

Anti-hENG mAbs SN6c, SN6d and SN6j were used to illustrate the antiangiogenic therapy according to the method of the present invention. Three sets of therapeutic protocols were used in the therapeutic study. In the first set of protocols, 4T1 murine breast cancer cells were inoculated subcutaneously (s.c.) into the flank of knockin mice stably expressing human/mouse chimeric ENG. Mice bearing palpable established tumors of a similar size were distributed evenly into four groups (n=7) at the onset of the therapy. Individual mice with established tumors in each group were treated by intravenous (i.v.) administration of 50 µg of SN6c, SN6d, SN6j or isotype-matched control IgG (MOPC 195v) via the tail vein. The administration was repeated at 3 or 4 days intervals (twice a week). Mice were followed daily, and tumor size and body weight were measured at 2 or 3 days interval (shown in FIG. 6A).

Figure 6B:
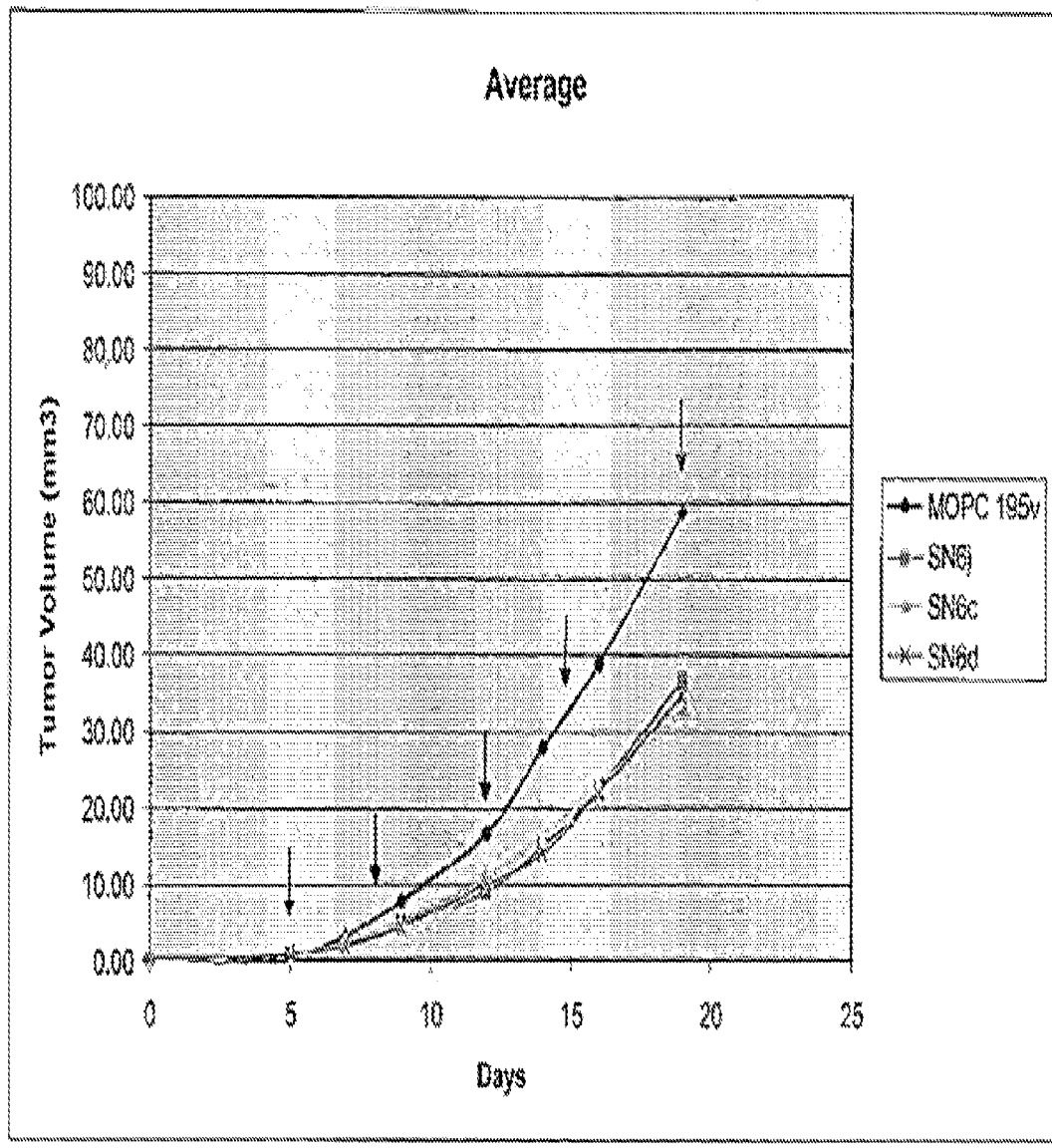
FIG. 6B depicts suppression of growth of established 4T1 tumors in knockin mice by intravenous administration of 100 μg of anti-hENG mAb SN6j, SN6c or SN6d. Experiment in this figure was performed in the same manner as that in FIG. 6A but 100 μg of mAb or control IgG were administered into individual knockin mice instead of 50 μg in FIG. 6A.

In the second set protocols, four groups knockin mice bearing established 4T1 tumors were generated and treated in a similar manner to the first protocol but by i.v. administraton of 100 µg of SN6c, SN6d, SN6j or control IgG (FIG. 6B).

Figure 7:
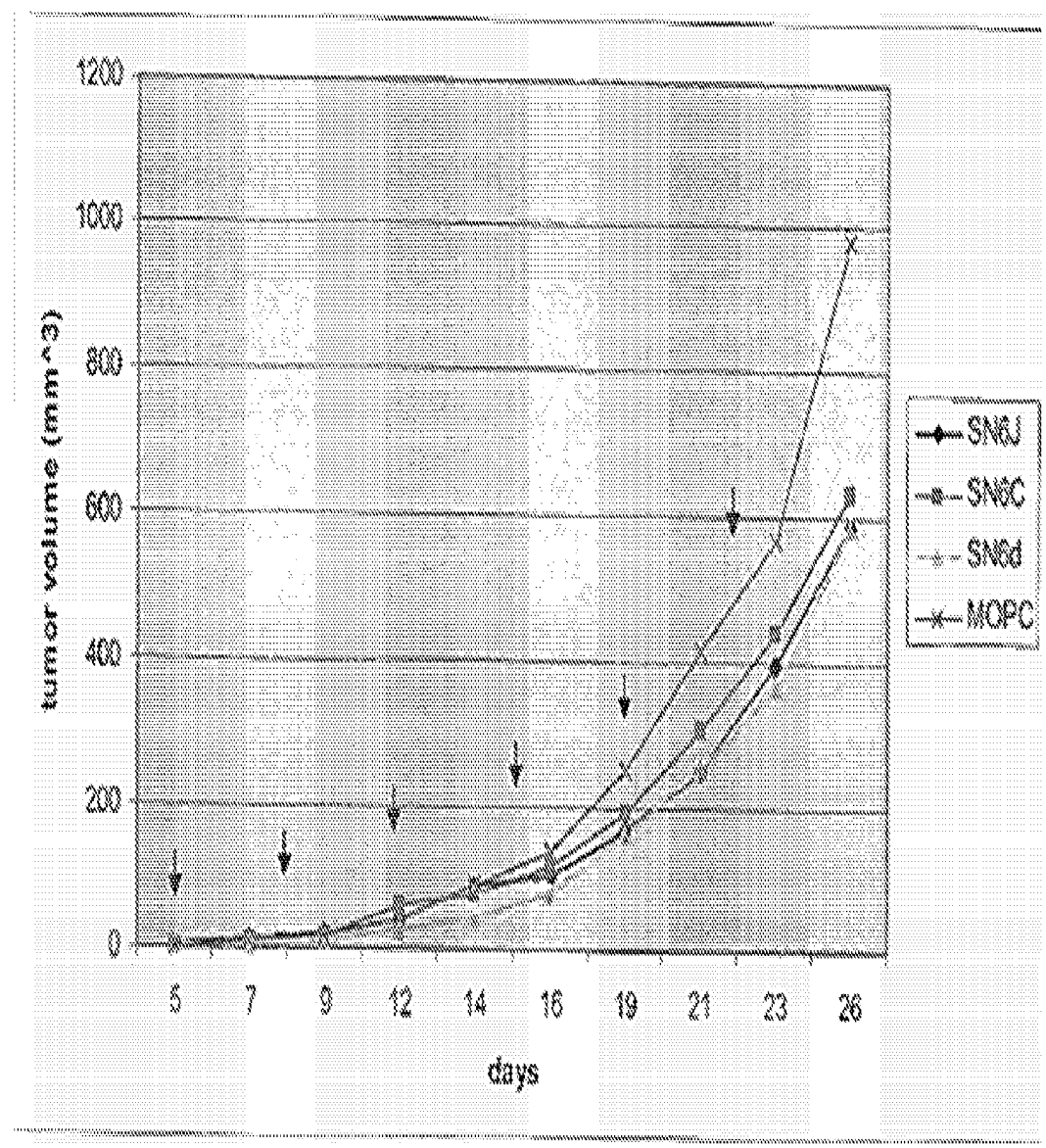
FIG. 7 depicts suppression of growth of established Col 26 colon tumors in knockin mice by anti-hENG mAbs. The mice bearing established subcutaneous tumors of Col 26 of a similar size were distributed evenly into four groups (n=6 for each group) at the onset of therapy. Individual mice with established tumors in each group were treated by intravenous administration of 100 μg of anti-hENG mAb SN6j, SN6c or SN6d, or an isotype-matched control IgG MOPC 195v (IgG1-κ). The administration was repeated at 3 or 4 days intervals (twice a week) as indicated by vertical arrows. Each graph line in the figure represents the average of tumor volumes of six mice in each group of mice. In addition to the difference in the tumor volume between anti-hENG mAb-treated groups and control IgG-treated group, three groups of mice treated with each of SN6j, SN6c and SN6d survived longer than the group treated with the control IgG.

In the third set of protocols, Col 26 murine colon cancer cells were inoculated s.c. into the flank of knockin mice. Mice bearing palpable established tumors of a similar size were distributed evenly into four groups (n=6) at the onset of the therapy. Individual mice with established tumors in each group were treated by i.v. administration of 100 µg of SN6c, SN6d, SN6j or isotype-matched control IgG. The administration was repeated at 3 or 4 days interval (twice a week). The mice were followed daily, and tumor size and body weight were measured at 2 or 3 day intervals. The results are shown in FIG. 7. When the survival of mice was followed, mice treated with the anti-hENG mAbs (SN6c, SN6d and SN6j) lived longer than those mice treated with control IgG.

Example 5

This Example provides a description of antiangiogenic therapy using chimeric and humanized anti-hENG mAbs. The mAbs raised against hENG as described above can also be made as chimeric antibodies, or they can be partially or fully humanized. Suitable techniques for making chimeric and humanized antibodies are well known in the art. A description of making and using chimeric and humanized antibodies is provided in U.S. Pat. No. 6,200,566, the entire disclosure of which is incorporated herein by reference. Methods for antiangiogenic therapies using chimeric and humanized anti-hENG mAbs are similar to those for using murine antibodies. In general, chimeric mAbs and humanized mAbs minimize the development of human anti-mouse antibody responses. Additionally, the chimeric or humanized antibodies generally change the pharmacokinetics by providing a longer half-life of the antibodies, as compared to the half-life of the parental murine antibody in human.

Example 6

This Example provides a description of epitope mapping for the antibodies described herein. To determine the steric epitopes of endoglin, we performed three different tests: 1) a sequential competitive inhibition test using several $^{125}$I-labeled SN6 series mAbs, 2) a simultaneous competitive binding assay, and 3) a comparison of the degrees of susceptibility of individual epitopes to various enzymatic digestions. The results of these tests are summarized graphically in FIG. 8.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. An isolated antibody or a fragment thereof, wherein the antibody or fragment thereof binds with specificity to a region of human endoglin between human endoglin amino acid Asn 121 and amino acid Ala 378, wherein the region of human endoglin between human endoglin amino acid Asn 121 and amino acid Ala 378 comprises the sequence of SEQ ID NO:9, and wherein the antibody is not cross-reactive with murine endoglin.

2. The antibody fragment thereof of claim 1, wherein the fragment is selected from the group consisting of Fab, Fab', (Fab')2, Fv, single chain (ScFv), and combinations thereof.

3. The antibody of claim 1, wherein the antibody is a chimeric or humanized antibody.

4. The antibody of claim 3, wherein the antibody is a humanized antibody comprising murine hypervariable regions having endoglin binding specificity for the region of human endoglin between human endoglin amino acid Asn 121 and amino acid Ala 378, and a constant region and variable region sequences of human immunoglobulin.

5. The antibody of claim 3, wherein the antibody is a chimerized antibody comprising murine variable regions having endoglin binding specificity for the region of human endoglin between human endoglin amino acid Asn 121 and amino acid Ala 378, and constant regions sequences of human immunoglobulin.

6. The antibody or fragment of claim 1, wherein the antibody or the fragment is conjugated to a cytotoxic agent.

7. A composition comprising the antibody or fragment thereof according to claim 1, wherein the composition comprises a pharmaceutically acceptable carrier.

* * * * *

SEQUENCE LISTING

<160> NUMBER OF SEQ ID NOS: 11

<210> SEQ ID NO 1
<211> LENGTH: 45
<212> TYPE: DNA
<213> ORGANISM: artificial sequence
<220> FEATURE:
<223> OTHER INFORMATION: primer

<400> SEQUENCE: 1
agaggaacca tggaaacagt ccattgtgac cttcagcctg tgggc          45

<210> SEQ ID NO 2
<211> LENGTH: 45
<212> TYPE: DNA
<213> ORGANISM: artificial sequence
<220> FEATURE:
<223> OTHER INFORMATION: primer

<400> SEQUENCE: 2
agaggaacca tgggtggtag gctgcagacc tcacccgcac cgatc          45

<210> SEQ ID NO 3
<211> LENGTH: 45
<212> TYPE: DNA
<213> ORGANISM: artificial sequence
<220> FEATURE:
<223> OTHER INFORMATION: primer

<400> SEQUENCE: 3
tcccgtcgac tattacaagt gcagtgggat tcccagggcc tggag          45

<210> SEQ ID NO 4
<211> LENGTH: 45
<212> TYPE: DNA
<213> ORGANISM: artificial sequence
<220> FEATURE:
<223> OTHER INFORMATION: primer

<400> SEQUENCE: 4
tcccgtcgac tattacccgg ccgagtggcc cggcaggacc ctcag          45

<210> SEQ ID NO 5
<211> LENGTH: 45
<212> TYPE: DNA
<213> ORGANISM: artificial sequence
<220> FEATURE:
<223> OTHER INFORMATION: primer

<400> SEQUENCE: 5
tcccgtcgac tattattctc cagtggtcca gatctgcatg ttgtg          45

<210> SEQ ID NO 6
<211> LENGTH: 45
<212> TYPE: DNA
<213> ORGANISM: artificial sequence
<220> FEATURE:
<223> OTHER INFORMATION: primer

<400> SEQUENCE: 6
tcccgtcgac tattagggtg aggtctgcag cctaccaccg cagct          45

<210> SEQ ID NO 7
<211> LENGTH: 45
<212> TYPE: DNA
<213> ORGANISM: artificial sequence
<220> FEATURE:
<223> OTHER INFORMATION: primer

<400> SEQUENCE: 7
tcccgtcgac tattagaaag agaggctgtc catgttgagg cagtg          45

<210> SEQ ID NO 8

```
<211> LENGTH: 48
<212> TYPE: DNA
<213> ORGANISM: artificial sequence
<220> FEATURE:
<223> OTHER INFORMATION: primer

<400> SEQUENCE: 8
tcccgtcgac tattagcctt tgcttgtgca accagacagg tcagggct            48

<210> SEQ ID NO 9
<211> LENGTH: 258
<212> TYPE: PRT
<213> ORGANISM: Human

<400> SEQUENCE: 9
```

Asn Ser Ser Leu Val Thr Phe Gln Glu Pro Gly Val Asn Thr Thr
1               5                   10                  15

Glu Leu Pro Ser Phe Pro Lys Thr Gln Ile Leu Glu Trp Ala Ala Glu
                20                  25                  30

Arg Gly Pro Ile Thr Ser Ala Ala Glu Leu Asn Asp Pro Gln Ser Ile
                35                  40                  45

Leu Leu Arg Leu Gly Gln Ala Gln Gly Ser Leu Ser Phe Cys Met Leu
50                  55                  60

Glu Ala Ser Gln Asp Met Gly Arg Thr Leu Glu Trp Arg Pro Arg Thr
65                  70                  75                  80

Pro Ala Leu Val Arg Gly Cys His Leu Glu Gly Val Ala Gly His Lys
                85                  90                  95

Glu Ala His Ile Leu Arg Val Leu Pro Gly His Ser Ala Gly Pro Arg
                100                 105                 110

Thr Val Thr Val Lys Val Glu Leu Ser Cys Ala Pro Gly Asp Leu Asp
                115                 120                 125

Ala Val Leu Ile Leu Gln Gly Pro Pro Tyr Val Ser Trp Leu Ile Asp
                130                 135                 140

Ala Asn His Asn Met Gln Ile Trp Thr Thr Gly Glu Tyr Ser Phe Lys
145                 150                 155                 160

Ile Phe Pro Glu Lys Asn Ile Arg Gly Phe Lys Leu Pro Asp Thr Pro
                165                 170                 175

Gln Gly Leu Leu Gly Glu Ala Arg Met Leu Asn Ala Ser Ile Val Ala
                180                 185                 190

Ser Phe Val Glu Leu Pro Leu Ala Ser Ile Val Ser Leu His Ala Ser
                195                 200                 205

Ser Cys Gly Gly Arg Leu Gln Thr Ser Pro Ala Pro Ile Gln Thr Thr
                210                 215                 220

Pro Pro Lys Asp Thr Cys Ser Pro Glu Leu Leu Met Ser Leu Ile Gln
225                 230                 235                 240

Thr Lys Cys Ala Asp Asp Ala Met Thr Leu Val Leu Lys Lys Glu Leu
                245                 250                 255

Val Ala

```
<210> SEQ ID NO 10
<211> LENGTH: 98
<212> TYPE: PRT
<213> ORGANISM: human

<400> SEQUENCE: 10
```

Ala Gln Gly Ser Leu Ser Phe Cys Met Leu Glu Ala Ser Gln Asp Met
1               5                   10                  15

```
Gly Arg Thr Leu Glu Trp Arg Pro Arg Thr Pro Ala Leu Val Arg Gly
            20                  25                  30

Cys His Leu Glu Gly Val Ala Gly His Lys Glu Ala His Ile Leu Arg
        35                  40                  45

Val Leu Pro Gly His Ser Ala Gly Pro Arg Thr Val Thr Val Lys Val
    50                  55                  60

Glu Leu Ser Cys Ala Pro Gly Asp Leu Asp Ala Val Leu Ile Leu Gln
65                  70                  75                  80

Gly Pro Pro Tyr Val Ser Trp Leu Ile Asp Ala Asn His Asn Met Gln
                85                  90                  95

Ile Trp

<210> SEQ ID NO 11
<211> LENGTH: 2669
<212> TYPE: DNA
<213> ORGANISM: human

<400> SEQUENCE: 11
```

| | | | | |
|---|---|---|---|---|
| actgcagatc caccagccag cattctcagc tccggcctct ttctctcagc caatgggctg | | | | 60 |
| actccacaaa ttacttcctg acctcctaca tgggatagag agggcacagg gccaggaaca | | | | 120 |
| gcgtgctgag cctccacatg tctccccaga attccagcct ggtcaccttc aagagcccc | | | | 180 |
| cgggggtcaa caccacagag ctgccatcct tccccaagac ccagatcctt gagtgggcag | | | | 240 |
| ctgagagggg ccccatcacc tctgctgctg agctgaatga ccccagagc atcctcctcc | | | | 300 |
| gactgggcca aggtcagttt ccccagcaac ctctctgggc tcatgatact gctcaggagg | | | | 360 |
| aatctgagct cctctggccc acacctcaaa cttgggcacc aagagtgcag gaggggacac | | | | 420 |
| gctgtgccac agttcacatg ccacaagcca gtgctgcctt gggacagtga tggctcctcc | | | | 480 |
| accaaatatc agattgaagc atgtggaata tgccaggttc tgacctaaaa ccccagcatt | | | | 540 |
| ttcatacgat ctattgtgca tctactatgt gccaaagccc tatcatgcta ggcacttggg | | | | 600 |
| gacacactca ggccctgcct tcctggagct gatactgtga tgagggaggt gacaataaac | | | | 660 |
| atgtacatgt acagagataa atctataatt tcgggtcttg ctgggtggtt tcggggctgc | | | | 720 |
| agcctaacat gtgtcatggg ctcatccctt atgttaacac acggaggccc gggaacttgc | | | | 780 |
| acagggtcac ttggcaggtg agtggtggaa gggaagttcg aacctaggtc tctctgacgcc | | | | 840 |
| tctccccctc tgcagcaccg tcctgcctgc ccaccacta tctttggctg tgggtgaggg | | | | 900 |
| cggggctctg ttaggtgcag ggctgctgag ggaagggact gaggtgcgcg tgtctctgca | | | | 960 |
| gcccaggggt cactgtccctt ctgcatgctg aagccagcc aggacatggg ccgcacgctc | | | | 1020 |
| gagtggcggc cgcgtactcc agccttggtc cggggctgcc acttggaagg cgtggccggc | | | | 1080 |
| cacaaggagg cgcacatcct gagggtcctg ccgggccact cggccgggta tggctctcgc | | | | 1140 |
| cccgcccctg acactagtcc ccaccccgag agaccacccc cctgaccccc ccgccccct | | | | 1200 |
| ctccggtccc ttataaagcc ccaccccagt cccagcccca gccccgccgc agccctgtga | | | | 1260 |
| gagcacagtc gctttctcct actctaggct acgccccta tgggcccctt ccctttgggc | | | | 1320 |
| acaagcctgg ccccagtccc atccctatcc cataaaccca cacctggcca ggtaagagtg | | | | 1380 |
| cagccgccgc ccacccgacg ccaggcctcg ctccccgcct ggcctgtccg cttcagtgtt | | | | 1440 |
| ccatccgcgt ctgtctcccc gcaggccccg gacggtgacg gtgaaggtgg aactgagctg | | | | 1500 |
| cgcacccggg gatctcgatg ccgtcctcat cctgcagggt ccccctacg tgtcctggct | | | | 1560 |
| catcgacgcc aaccacaaca tgcagatctg ggtgagttgt gcgcagctcc cgggacacaa | | | | 1620 |

```
aacccaaact cccaacctct ggatcaggga agtttcctgg aaaggtgaac ccccgagctg    1680
agctgaagga caaatcacct atgcccatac gtgagggaag gggccaggca gaagacgcag    1740
caggagtggg gacacagcag gaccgaggcc tggcataacc ctggctggcc tgctgtggca    1800
cagactgtgt ccatggcccc ctgttctgcc tctctcccca ccattagacc actggagaat    1860
actccttcaa gatctttcca gagaaaaaca ttcgtggctt caagctccca gacacacctc    1920
aaggcctcct gggggaggcc cggatgctca atgccagcat tgtggcatcc ttcgtggagc    1980
taccgctggc cagcattgtc tcacttcatg cctccagctg cggtgagcac ccttcccctg    2040
cccctccctt cccttcccct cccttggatc agtggccaca ctgttggtga agcacctctg    2100
tgtgagcttg ggcaaggtac atcagcctct ctgagcctca tttttctcat ctgcacatgg    2160
gaacaatggg agtagctaat catagaagag cctgagaatc gcttgaacct gggagatgga    2220
ggttgcagtg agccaagatc gtgccactgc actccagccc gggtaacaga gcaaaactcc    2280
gtctcaaaaa aaaaaaaaaa aaaaaaaaag cctggtgcgg gcacacagtg atcacacagt    2340
gaccagccgc ctggcctgcc tctgctaccc cacaggtggt aggctgcaga cctcaccccgc   2400 accgatccag accactcctc ccaaggacac ttgtagcccg gagctgctca tgtccttgat    2460
ccagacaaag tgtgccgacg acgccatgac cctggtacta aagaaagagc ttgttgcggt    2520
aagggaactc ctgcccctct ggctcaggat gacatggaca tctggttcct cccctagccc    2580
aagactcttg gggtcctagc ccaggcaggg gggcaagtca cgtccctctg caagccttag    2640
ttttcccact tgtataatgg aattgataa                                     2669
```